US006664369B1

(12) United States Patent
Lovas et al.

(10) Patent No.: US 6,664,369 B1
(45) Date of Patent: Dec. 16, 2003

(54) GNRH ANALOGUES WITH ANTITUMOUR EFFECTS AND PHARMACEUTICAL COMPOSITIONS THEREOF

(75) Inventors: Sandor Lovas, Omaha, NE (US); Richard F. Murphy, Omaha, NE (US); Geza Toth, Szeged (HU); Adrienn Kalnay, Budapest (HU); Istvan Palyi, Budapest (HU); Gizella Turi, Budapest (HU); Borbala Vincze, Budapest (HU); Imre Mezom, Budapest (HU); Zsolt Vadasz, Budapest (HU); Istvan Teplan, Budapest (HU); Janos Seprodi, Budapest (HU); Melinda Mora, Budapest (HU)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 09/269,954

(22) PCT Filed: Aug. 9, 1995

(86) PCT No.: PCT/US95/10054

§ 371 (c)(1),
(2), (4) Date: Jul. 27, 2000

(87) PCT Pub. No.: WO96/04927

PCT Pub. Date: Feb. 22, 1996

(30) Foreign Application Priority Data

| Oct. 8, 1994 | (HU) | P 94 02329 |
| Oct. 8, 1994 | (HU) | P 94 02328 |

(51) Int. Cl.$^7$ .............................................. C07K 7/06
(52) U.S. Cl. ........................................ 530/328; 514/15
(58) Field of Search ............................ 530/328; 514/15

(56) References Cited

U.S. PATENT DOCUMENTS

| 3,871,964 A | 3/1975 | Hüper et al. ................ 195/63 |
| 4,116,742 A | 9/1978 | Firth ........................... 156/289 |
| 4,424,079 A | 1/1984 | Barabas ........................ 134/4 |
| 4,833,166 A | 5/1989 | Grosvenor et al. ........... 514/12 |
| 4,975,420 A | 12/1990 | Silversides et al. .......... 514/15 |
| 5,593,965 A | 1/1997 | Lovas et al. ................. 514/15 |

FOREIGN PATENT DOCUMENTS

| EP | 0 368 449 A2 A3 | 5/1990 |
| HU | 34519 | 3/1985 |
| HU | 212 661 A | 11/1996 |
| HU | 212 662 A | 11/1996 |
| JP | 9-508142 | 8/1997 |
| WO | WO 96/04927 | 2/1996 |

OTHER PUBLICATIONS

"Breast Cancer," American Cancer Society [online]. [Retrieved Mar. 18, 1996].Retrieved from the Internet: <URL:http://www.cancer.org/breast.html>, 2 pages.

Creighton University, "Creighton Scientists and Hungarian Partners Develop Promising Therapy for Breast and Prostate Cancers," Creighton University Public Relations Department Press Release, 2 pages (Mar. 31, 1999).

Abstract of Nishida et al., "Establishment of a New Human Endometrial Adenocarcinoma Cell Line, Ishikawa Cells, Containing Estrogen and Progesterone Receptors," Japanese language journal article with English language synopsis, *Acta Obstetrica et Gynaecologica Japonica*, 37(7):1103–1111 (1985).

"Table 1. Breast Cancer incidence in women in Australia, 1990," National Breast Cancer Centre, National Health and Medical Research Council [online]. Sydney, Australia, Oct. 11, 1995 [retrieved Mar. 18, 1996]. Retrieved from the Internet: <URL:http://www.nbcc.org.au/pages/table1.htm>, 1 page.

"Table 2. Breast Cancer Incidence Worldwide," National Breast Cancer Centre, National Health and Medical Research Council [online]. Sydney, Australia, Oct. 10, 1995 [retrieved Mar. 23, 1996]. Retrieved from the Internet: <URL: http://www.nbcc.org.au/pages/table2.htm>, 1 page.

"Table 3. Estimates of breast cancer incidence and mortality in women in some countries of the European Union and in Australia," National Breast Cancer Centre, National Health and Medical Research Council [online]. Sydney, Australia, Oct. 11, 1995 [retrieved Mar. 18, 1996]. Retrieved from the Internet: <URL: http://www.nbcc.org.au/pages/table3.htm>, 1 page.

Glass, John, D., "Enzymatic Manipulation of Protecting Groups in Peptide Synthesis," *The Peptides*, Udenfriend et al., eds., Academic Press, Inc., San Diego, Title page, publication page, table of contents, pp. 178 and 253 (1987).

National Center for Biotechnology Information, National Library of Medicine, National Institutes of Health, GenBank Accession No. AAB25536, "Gonadotropin–releasing hormone, GnRH–III [Petromyzon marinus=sea lampreys, brain, Peptide, 10 aa]," [online]. Bethesda, MD [retrieved on Jun. 20, 2001]. Retrieved from the Internet:<URL: http://www.ncbi.nlm.nih.gov/entrez/query.fcgi?cmd+Retrieve&db=Protein&list_uids=266203&dopt=DocSum, 1 page.

Azori et al., "Synthesis, elimination, and whole–body distribution of $^{14}$C–labelled drug carrier," *Die Makromolekulare Chemie*, 187(2):297–302 (1986).

(List continued on next page.)

Primary Examiner—Christopher S. F. Low
Assistant Examiner—David Lukton
(74) Attorney, Agent, or Firm—Mueting, Raasch & Gebhardt, P.A.

(57) ABSTRACT

The present invention provides peptides and pharmacologically active compounds including gonadotropin-releasing hormone (GnRH) analogues according to formulas of the invention, wherein the compounds show an antitumor effect. The invention additionally provides compositions including these peptides and compounds.

2 Claims, No Drawings

OTHER PUBLICATIONS

Bokser et al., "Inhibition of pituitary–gonadal axis in mice by long–term administraiton of D–Trp–6–LHRH microcapsules," *Journal of Reproduction and Fertility*, 85(2):569–574 (1989).

Butler, "Synthesis and Properties of Novel Polyanions of Potential Antitumor Activity," *Journal of Macromolecular Science—Chemistry*, A13(3):351–368 (1979).

Cailleau et al., "Breast Tumor Cell Lines From Pleural Effusions," *Journal of the National Cancer Institute*, 53(3):661–674 (1974).

Edsall et al., eds., "IUPAC–IUB Combined Commission on Biochemical Nomenclature Abbreviations and Symbols for Chemical Names of Special Interest in Biological Chemistry, Revised Tentative Rules (1965)," *Journal of Biological Chemistry*, 241(3):527–533 (1966).

Eidne et al., "Gonadotropin–Releasing Hormone Binding Sites in Human Breast Carcinoma," *Science*, 229(4717):989–991 (1985).

Eidne et al., "Gonadotropin–Releasing Hormone (GnRH)–Binding Sites in Human Breast Cancer Cell Lines and Inhibitory Effects of GnRH Antagonists," *Journal of Clinical Endocrinology and Metabolism*, 64(3):425–432 (1987).

Gaál et al., "Immunomodulatory Effect of Synthetic Branched Polypeptides. II.," *Journal of Biological Response Modifiers*, 5(2):148–159 (1986).

Gros, "Biological Activity," *Encyclopedia of Polymer Science and Engineering*, vol. 2, John Wiley & Sons, Inc., New York, Title page, publication page, and pp. 243–267 (1985).

Harris et al., "Gonadotropin–releasing Hormone Gene Expression in MDA–MB–231 and ZR–75–1 Breast Carcinoma Cell Lines," *Cancer Research*, 51(10):2577–2581 (1991).

Holden, ed., "Tamoxifen Labeled Carcinogen," *Science*, 271(5254):1367 (1996).

Kaighn et al., "Establishment and characterization of a human prostatic carcinoma cell line (PC–3)," *Investigative Urology*, 17(1):16–23 (1979).

Kálnay et al., "Influence on antiproliferative activity of structural modification and conjugation of gonadotropin–releasing hormone (GnRH) analogues," *Cell Proliferation*, 33(5):275–285 (Oct., 2000).

Kaufmann et al., "Goserelin, a Depot Gonadotropin–Releasing Hormone Agonist in the Treatment of Premenopausal Patients With Metastatic Breast Cancer," *Journal of Clinical Oncology*, 7(8):1113–1119 (1989).

King et al., "Structure of Chicken Hypothalamic Luteinizing Hormone–releasing Hormone: I. Structural Determination on Partially Purified Material," *Journal of Biological Chemistry*, 257(18):10722–10728 (1982).

Kovács et al., "Effects of Long–Term Administration of a Superactive Agonistic and an Antagonistic GnRH Analog on the Pituitary–Gonad System," *Peptides*, 10(5):925–931 (1989).

Limonta et al., "Expression of luteinizing hormone–releasing hormone mRNA in the human prostatic cancer cell line LNCaP," *Journal of Clinical Endocrinology and Metabolism*, 76(3):797–800 (1993).

Maeda et al., "Conjugation of Poly(styrene–co–maleic acid) Derivatives to the Antitumor Protein Neocarzinostatin: Pronounced Improvements in Pharmacological Properties," *Journal of Medicinal Chemistry*, 28(4):455–461 (1985).

Mezö et al., "GnRH analogs and their conjugates with enhanced antitumor activity," Proceedings of the Twenty Third European Peptide Symposium, Sep. 4–10, 1994, Braga, Portugal, *Peptides 1994*, pp. 763–764 (1995).

Mezo et al., "GnRH analogs and their conjugates with enhanced antitumor activity," Proceedings of the European Peptide Symposium, Sep. 23, 1994, *Peptides*, pp. 763–764, *Chemical Abstracts*, 125(25): abstract no. 316399 (1996).

Mezö et al., "Synthesis, Conformation, Biodistribution, and Hormone–Related in Vitro Antitumor Activity of a Gonadotropin–Releasing Hormone Antagonist–Branched Polypeptide Conjugate," *Bioconjugate Chemistry*, 7(6):642–650 (1996).

Mezö et al., "Properties of GnRH conjugates in vivo," Proceedings of the Fifteenth American Peptide Symposium, Jun. 14–19, Nashville, *Peptides: Frontiers of Peptide Science*, Tam et al., eds., Kluwer Academic Publishers, Boston, pp. 561–562 (1997).

Mezö "Synthesis of Gonadotropin–Releasing Hormone III Analogs. Structure–Antitumor Activity Relationships," *Journal of Medicinal Chemistry*, 40(21):3353–3358 (1997); published erratum in *Journal of Medicinal Chemistry*, 41(11):1996 (1998).

Néri et al., "Compared effects of GnRH analogs and 4–hydroxytamoxifen on growth and steroid receptors in antiestrogen sensitive and resistant MCF–7 breast cancer cell sublines," *Breast Cancer Research and Treatment*, 15, (2):85–93 (1990).

Ottenbrite, "Antitumor Activity of Polycarboxylic Acid Polymers," *Journal of Macromolecular Science–Chemistry*, A22(5–7):819–832 (1985).

Pályi et al., "Gonadotropin–releasing hormone analogue conjugates with strong selective antitumour activity," *Proceedings of the National Academy of Sciences USA*, 96(5):2361–2366 (Mar. 2, 1999).

Reddy et al., "Preparation of potentially electroactive thallium polymers derived from the acidic copolymers of maleic anhydride," *Polymer*, 25(1):115–120 (1984).

Schally, "The use of LHRH analogs in gynecology and tumor therapy," *General Gynecology*, vol. 6, Belfort et al., eds., Parthenon Publishing, Carnforth, England, Title page, publication page, table of contents, and pp. 3–22 (1989).

Scott et al., "Factors Influencing the Response of MCF–7 Cells to an Agonist of Luteinising Hormone–releasing Hormone," *European Journal of Cancer*, 27(11):1458–1461 (1991).

Segal–Abramson et al., "Guanine nucleotide modulation of high affinity gonadotropin–releasing hormone receptors in rat mammary tumors," *Molecular and Cellular Endocrinology*, 85(1–2):109–116 (1992).

Segal–Abramson et al., "Direct effects of luteinizing hormone–releasing hormone agonists and antagonists on MCF–7 mammary cancer cells," *Proceedings of the National Academy of Sciences USA*, 89(6):2336–2339 (1992).

Sharoni et al., "Inhibition of growth of human mammary tumor cells by potent antagonists of luteinizing hormone–releasing hormone," *Proceedings of the National Academy of Sciences USA*, 86(5):1648–1651 (1989).

Sherwood et al., "Characterization of a teleost gonadotropin–releasing hormone," *Proceedings of the National Academy of Sciences USA*, 80(9):2794–2798 (1983).

Soule et al., "A Human Cell Line From a Pleural Effusion Derived From a Breast Carcinoma," *Journal of the National Cancer Institute*, 51(5):1409–1416 (1973).

Sower et al., "Primary Structure and Biological Activity of a Third Gonadotropin–Releasing Hormone from Lamprey Brain," *Endocrinology*, 132(3):1125–1131 (1993).

Steel et al., "Improved Immune–Suppression Techniques for the Xenografting of Human Tumours," *British Journal of Cancer*, 37(2):224–230 (1978).

Szepeshazi et al., "Growth inhibition of estrogen independent MXT mouse mammary carcinomas in mice treated with an agonist or antagonist of LH–RH, an analog of somatostatin, or a combination," *Breast Cancer Research and Treatment*, 21(3):181–192 (1992).

Tabor et al., eds., "IUPAC–IUB Commission on Biochemical Nomenclature Symbols for Amino–Acid Derivatives and Peptides, Recommendations (1971)," *Journal of Biological Chemistry*, 247(4):977–983 (1972).

Vincze et al., "Effect of LHRH agonist on estradiol sensitive and insensitive human breast cancer cells," Abstract A4.116.04, 15$^{th}$ International Cancer Congress, Hamburg, Aug. 16–22, *Journal of Cancer Research and Clinical Oncology*, 116427 (1990).

Vincze et al., "Influence of luteinizing hormone–releasing hormone agonists on human mammary carcinoma cell lines and their xenografts," *Journal of Steroid Biochemistry and Molecular Biology*, 38(2):119–126 (1991).

Vincze et al., "Direct effect of GNRH agonists and antagonists on estradiol–dependent and –independent human mammary cancer cells," Abstract, *Cell Proliferation*, 25:518 (1992).

Vincze et al., "Antitumour effects of a gonadotropin–releasing–hormone antagonist (MI–1544) and its conjugate on human breast cancer cells and their xenografts," *Journal of Cancer Research and Clinical Oncology*, 120:578–584 (1994).

Weinbauer et al., "LH–RH Antagonists: State of the Art and Future Perspectives," *Recent Results in Cancer Research*, 124:113–136 (1992).

Yano et al, "Inhibition of growth of MCF–7 MIII human breast carcinoma in nude mice by treatment with agonists or antagonists of LH–RH," *Breast Cancer Research and Treatment*, 21(1):35–45 (1992).

SEQUENCE LISTING

<160> NUMBER OF SEQ ID NOS: 6

<210> SEQ ID NO 1
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: SITE
<222> LOCATION: (10)..(10)
<223> OTHER INFORMATION: Gly-NH2

<400> SEQUENCE: 1

Xaa His Trp Ser Tyr Gly Leu Arg Pro Xaa
1               5                   10

<210> SEQ ID NO 2
<211> LENGTH: 10
<212> TYPE: PRT
<213> ORGANISM: Petromyzon marinus
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: SITE
<222> LOCATION: (10)..(10)
<223> OTHER INFORMATION: Gly-NH2

<400> SEQUENCE: 2

Xaa His Trp Ser His Asp Trp Lys Pro Xaa
1               5                   10

<210> SEQ ID NO 3
<211> LENGTH: 10
<212> TYPE: PRT
<213> ORGANISM: Artificial
<220> FEATURE:
<223> OTHER INFORMATION: GnRH analogue
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: SITE
<222> LOCATION: (10)..(10)
<223> OTHER INFORMATION: Gly-NH2

<400> SEQUENCE: 3

Xaa His Trp Ser His Asp Trp Lys Pro Xaa
1               5                   10

<210> SEQ ID NO 4
<211> LENGTH: 10
<212> TYPE: PRT
<213> ORGANISM: Artificial
<220> FEATURE:
<223> OTHER INFORMATION: GnRH analogue
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: SITE
<222> LOCATION: (10)..(10)
<223> OTHER INFORMATION: Gly-NH2

```
<400> SEQUENCE: 4

Xaa His Trp Ser Tyr Gly Leu Arg Pro Xaa
1               5                   10

<210> SEQ ID NO 5
<211> LENGTH: 4
<212> TYPE: PRT
<213> ORGANISM: Artificial
<220> FEATURE:
<223> OTHER INFORMATION: Spacer moiety
<220> FEATURE:
<221> NAME/KEY: SITE
<222> LOCATION: (1)..(1)
<223> OTHER INFORMATION: H-Gly
<220> FEATURE:
<221> NAME/KEY: SITE
<222> LOCATION: (4)..(4)
<223> OTHER INFORMATION: Gly-OH

<400> SEQUENCE: 5

Xaa Phe Leu Xaa
1

<210> SEQ ID NO 6
<211> LENGTH: 10
<212> TYPE: PRT
<213> ORGANISM: Artificial
<220> FEATURE:
<223> OTHER INFORMATION: GnRH analogue
<220> FEATURE:
<221> NAME/KEY: MOD_RES
<222> LOCATION: (1)..(1)
<223> OTHER INFORMATION: PYRROLIDONE CARBOXYLIC ACID
<220> FEATURE:
<221> NAME/KEY: SITE
<222> LOCATION: (6)..(6)
<223> OTHER INFORMATION: D-Trp
<220> FEATURE:
<221> NAME/KEY: SITE
<222> LOCATION: (10)..(10)
<223> OTHER INFORMATION: Gly-NH2

<400> SEQUENCE: 6

Xaa His Trp Ser Tyr Xaa Leu Arg Pro Xaa
1               5                   10
```

GNRH ANALOGUES WITH ANTITUMOUR EFFECTS AND PHARMACEUTICAL COMPOSITIONS THEREOF

BACKGROUND OF THE INVENTION

1. Field of the Invention

The present invention relates generally to the fields of biochemical endocrinology and anti-neoplastic pharmacology. More specifically, the present invention relates to novel GnRH analogues having antitumour effects and pharmaceutical compositions thereof.

2. Description of the Related Art

It is known that this factor of hypothalamic origin (a peptide hormone built up of 10 amino acids) is responsible for the secretion of luteinizing hormone (LH) and follicle-stimulating hormone (FSH). A number of agonistic and antagonistic analogues of GnRHs proved to be not only useful for the successful influencing of processes of the reproduction biology but also suitable as antitumour drugs.

GnRH analogues can exert their antitumour effect not only through chemical castration but also in a selective way by directly acting on the tumour cells. The presence of receptor(s) specifically binding GnRH or GnRH analogues, respectively, as well as that of GnRH-mRNA were shown in cell cultures of cancers of human mammary, prostate, ovary and pancreas. Furthermore, the in vitro proliferation-inhibiting action of GnRH analogues was proven on the same cell lines. The specific binding of tritium-labelled D-Phe$^6$-GnRH(1-9)-ethylamide (OVURELIN), a human GnRH superagonist, to cells of MCF-7 and MDA-MB-231 human mammary carcinoma cell lines was demonstrated in experiments. These results confirm the presence of receptor(s) specifically binding GnRH analogues, which is a fundamental condition for development of a direct effect. Similarly, D-Trp$^6$-hGnRH (DECAPEPTYL), an agonistic analogue brought into the therapeutical practice, proved to possess a receptor on the MDA-MB-231 tumour cell line and a direct growth-inhibiting effect on the human mammary tumour cell line mentioned above.

Based on the effective concentration it can be supposed that low-affinity binding site or sites may play an important role in the development of direct antitumour effect. According to the literature the direct antitumour action of GnRH analogues occurs only at relatively high peptide concentrations ($10^{-6}$–$10^{-5}$ M). This pharmacological effect can be achieved only in the case when the active molecule is present in the body not only in a high concentration but also for a long time. For a long time, GnRH was not believed to be a species-specific hormone; it has become known as late as in the early 80's that the structure of gonadoliberin of some fish and bird species, respectively, is different from that of the mammals. In comparison to the mammalian GnRH, the structure of fish- and bird-specific GnRH, respectively, differs in the amino acid position(s) 7 and/or 8. In relation to the release of LH and FSH, respectively, of mammals, the analogues of chicken GnRH or salmon GnRH are not hyperactive and therefore, they do not desensitize the gonadotropic cells of hypophysis in the corresponding dose range. The composition of mammalian, e.g. human, GnRH is as follows: pGlu-His-Trp-Ser-Tyr-Gly-Leu-Arg-Pro-Gly-NH$_2$ (SEQ ID NO:1).

In 1993, researchers isolated and synthesized the Lamprey-III-GnRH decapeptide from lamprey (Petromyzon marinus) (pGlu-His-Trp-Ser-His-Asp-Trp-Lys-Pro-Gly-NH$_2$ (SEQ ID NO:2)). This Lamprey-III-GnRH (herein below GnRH-III) exerts a significant tumour growth-inhibiting effect on human mammary tumour cell lines. Simultaneously, on investigating the endocrinological effect of GnRH-III on rat hypophysis by using the superfusion method it has been found that the LH-releasing effect of this hormone is about thousand times weaker than that of the human GnRH. In the course of in vivo investigations it has been found that, during a prolonged treatment for three cycles, it did not inhibit the ovulation of female rats even in high doses; therefore, it did not induce desensitisation and chemical castration. In relation thereto, a "flair up" tumour growth occurring at the beginning of treatment did not appear on the tumour-bearing animals in contrast to other known human hormone analogues acting through the same mechanism of action. Thus, GnRH-III is a selective, highly active antitumour compound.

During the therapeutical use of peptide hormones and their synthetic analogues, a frequent demand is to retain the amount of the pharmacologically active molecule at a high and steady level. Thus, e.g. several agonistic and antagonistic synthetic analogues of gonadoliberin (GnRH), a peptide hormone built up from ten amino acids stimulating the release of luteinizing hormone (LH) and follicle-stimulating hormone (FSH) from the hypophysis, proved to be useful not only for successfully influencing processes of reproduction biology but also to provide the possibility of use as antitumour drugs. Depending on the way of use, GnRH and its analogues are able to stimulate or inhibit the secretion of gonadotropin. On carrying out a treatment repeatedly or continuously for a prolonged time with GnRH analogues, a so-called pharmacological gonadectomy is induced as a result of a desensitizing effect exerted on the hypophysis by a pronounced reduction of release of gonadotropin and steroids. Gonadectomy is a required therapeutical intervention in the treatment of steroid-dependent gonadal disease-entities. Simultaneously, gonadectomy is reversible and does not psychically disturb the patient. These analogues proved to be effective in the therapy of prostate, mamma and endometrium carcinomas and even cancers of pancreas and hypophysis on the basis of most recent data. Synthetic-GnRH antagonists are derivatives competitively inhibiting the native hormone. In the case of potent antagonists the amino acids in positions 1 to 3, 6 and 10 are usually exchanged for non-coded amino acids, e.g. of D-configuration. The anti-ovulatory effect of GnRH antagonists is well known. The GnRH analogues may exert their antitumour action not only through chemical castration but also through a direct effect on the tumour cells. Eidne et al. [J. Clin. Endocrinol. Metab. 64, 423–432 (1987)] demonstrated the presence of low-affinity binding sites in the cell cultures of MCF-7 and MDA-MB-231 human mammary tumours; based on the direct inhibitory effect of antagonistic analogues they concluded that GnRH behaves as an autocrine regulatory factor in mammary carcinoma cells. Results most recently published in the literature confirm the expression of GnRH gene in mammary carcinoma cells, which likely occurs during lactation and malignant transformation [Harris et al.: Cancer Res. 51, 2577–2581 (1991)]. The presence in the neoplastic tissue of GnRH-binding sites supports that GnRH has very probably an immediate palliative effect in the therapy of patients suffering from mammary carcinoma. Human mammary carcinoma cell lines or xenografts developed therefrom are useful in vitro and in vivo model systems for demonstrating the direct action of GnRH. GnRH agonists, when administered alone in substance form, are proteolytically decomposed and rapidly eliminated; thus, a steady and high GnRH analogue level, required for development of a direct or indirect antitumour effect, cannot be achieved. The retention of a high and steady level required for the inhibition of the tumour can be solved by a very frequent administration (daily several times) or by means of pharmaceutical compositions with prolonged effect. Up to the present, the microcapsule or microgranular form of GnRH analogues has been used for tumour inhibition in the clinical practice (Buserelin retard® and Decapeptyl retard® agonistic compositions).

According to another method to achieve a prolonged effect the pharmacologically active molecule is chemically coupled to molecules (e.g. polymers) slowly eliminating from the body. Conjugates thus obtained slowly diffuse in biological systems and alter the distribution in the body and absorption properties of the active agent. Thus, targeted transport of the pharmacologically active molecule and the reduction of undesired side effects can also be attained.

Preferred carriers are the water-soluble native and synthetic polymers, first of all homo- or copolymers, respectively, of carboxylic acids as synthetic polymers. Styrene/maleic anhydride copolymer- has a molecular weight of about 1600 to 2000 D, consisting of 7 to 8 styrene/maleic anhydride units wherein maleic anhydride had partially been hydrolyzed or esterified, respectively, was successfully used for improvement of the pharmacological properties of neo carcinostatin. In this way a more favourable distribution in the body together with a reduction of toxicity of the active agent could be achieved [H. Maeda et al.: J. Med. Chem. 28, 455–461 (1985)].

Polyanionic macromolecules with higher molecular weight may also possess themselves biological activity (e.g. antitumour, immunoadjuvant, interferon-inducing effects). However, their molecular weight and the distribution of the molecular weight proved to be crucial, i.e. their toxicity was increased by the increase in the molecular weight [L. Gros: Encyclopedia of Polymer Science and Technology, Vol. 2, pp. 243–267; as well as G. Butler: J. Macromol. Sci. Chem. A13, 351–368 (1979); and R. Ottenbrite: ibid. A22, 819–832 (1985)].

Thus, such polymers can be considered as carrier molecules that can be prepared with a good reproducibility, small polydispersity, which are not toxic and are eliminated at an optimum rate from the body. It is also important that the pharmacologically active molecules be capable of being coupled with a good reproducibility to these polymers to obtain a product with an appropriate solubility in water and the desired pharmacological activity.

Up to the present, peptide hormones and within these GnRH or GnRH analogues have not been coupled to known polycarboxylic acids as carriers. Copolymers prepared from vinylpyrrolidone and maleic anhydride are described in the Hungarian patent specification No. 194,286 (Hungarian patent publication No. 34519). These copolymers were prepared for cosmetical use; they are very useful skin-cosmetics and can be employed both in hydrophilic as well as lipophilic type emulsions. Depending on the amount of the base added, the pH value of their aqueous solutions can be varied within wide limits, they possess a high buffer capacity and can be prepared with a narrow range of polydispersity and with a good reproducibility. The vinylpyrrolidone and maleic anhydride units are incorporated to the molecule in a 1:1 molar ratio, with an alternating sequence.

Earlier, the toxicity, elimination and body distribution of the N-vinyl-pyrrolidone/maleic acid copolymer (NVP-MA) had been investigated in detail and the following statements were made [M. Azori et al: Macromol. Chem. 187, 297–302 (1986)]. On the intraperitoneal or intravenous, respectively, administration of the polymer (with an average molecular weight of 20,000) in the form of its sodium salt of pH 7.2, no death occurred up to 900 mg/kg of body weight in the first case (i.p.) or up to 200 mg/kg of body weight dose, respectively, in the second case (i.v.). This indicates that NVP-MA is less toxic than many other polyanions having a similar structure. [The intravenous (i.v.) $LD_{50}$ value of a divinyl ether/maleic acid copolymer with similar molecular weight is 74 mg, that of polymaleic acid is 110 mg and that of furan/maleic acid copolymer amounts to 130 mg.] Body distribution examinations carried out with a $^{14}C$-labelled polymer (having an average molecular weight of 8000) indicated that the polymer cannot enter the brain and spinal cord. The polymer is eliminated mainly in the urine: 84% of the radioactivity introduced were eliminated during 24 hours whereas after 56 hours altogether 95% of the radioactivity introduced could be detected in the urine and feces. NVP-MA and its known derivatives until now have not been used in the therapy but on the basis of their favourable properties it seems possible to introduce them into the body without toxic effects.

The prior art is still deficient in the lack of effective means of inhibiting the wide variety of neoplastic conditions. The present invention fulfills this longstanding need and desire in the art.

SUMMARY OF THE INVENTION

The invention relates to novel, pharmacologically active compounds of general formula (I), their salts and complexes as well as to a process for preparing same. In the general formula (I)

Y means the molecular moiety of general formula (Ia),

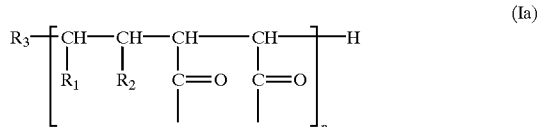

wherein n is an integer from 10 to 400, preferably 20 to 200; one of $R_1$ and $R_2$ stands for hydrogen whereas the other one means a group of formula (B),

$R_3$ means a polymeriation-initiating group, preferably $(CH_3)_2CCN$ group;

W means a hydroxyl group, optionally as a salt formed with an alkali metal ion, preferably sodium ion;

V represents a C1–8, preferably C4–6, alkylamino group bonded through its amino group; or a valence bond;

X means an amino acid group or an oligopeptide group of at most six members wherein the amino acid or oligopeptide group is coupled through its N-terminal to the Y group and is optionally bearing a hydroxyl group or a valence bond on its C-terminal, wherein the amino acids are Gly, Ala, Leu, Ile, Val, Phe, Tyr, Ahx, Pro, Arg or His;

A is present and represents a pharmacologically active polypeptide hormone group containing an amino group and directly coupled therethrough to the Y group when r is 0; or coupled to the C-terminal of the X group, respectively, when r is larger than 0;

r is an integer from 0 to 0.2 n;

k is an integer being at most equal to r;

z is an integer from 0 to (n−r); and u is an integer from n to 2n−r−z, as well as the salts and complexes of these compounds.

The invention furthermore relates to the novel intermediates of general formula (Ic), $$Y[W_u, V'_z, (XOQ)r] \qquad (Ic)$$

wherein

Y means the molecular moiety of general formula (Ia), wherein n is an integer from 10 to 400, preferably 20 to 200; one of $R_1$ and $R_2$ stands for hydrogen atom whereas the other one means a group of formula (B);

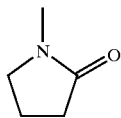
(B)

$R_3$ means a polymerization-initiating group, preferably $(CH_3)_2CCN$ group;

W means a hydroxyl group, optionally as a salt formed with an alkali metal ion, preferably sodium ion;

V' stands for a C1–8, preferably C4–6, alkylamino group bonded through its amino group;

X represents an amino acid group or an oligopeptide group of at most six members coupled through its N-terminal to the Y group;

OQ means an activated ester group on C-terminal of the X group, preferably

ONp, OPcp, OPfp or ONSu group;

r is an integer from 0 to 0.2 n;

z is an integer from 0 to (n−r); and u is an integer from n to (2n−r−z), as well as the salts of these compounds.

Furthermore, the invention relates to tumour-inhibiting and immunostimulatory pharmaceutical compositions comprising as active ingredient a compound of general formula (I). The bioconjugates of general formula (I) possess a selective tumour-inhibiting effect; a part of the compounds of general formula (I) inhibit the growth of both steroid-dependent and steroid-independent tumours, particularly mammary carcinomas. The compounds of general formula (I) show the effect of the pharmacologically active moiety in an increased and prolonged degree.

The invention relates to novel peptides possessing antitumour effect as well as their salts and esters. In addition to antiestrogens, gonadotropin-releasing hormone (GnRH) analogues play an important role in the treatment of hormone-dependent malignant tumours. Within the malignant neoplasms, the scope of their use extends to the cancers of prostate, breast (mammary), endometrium and other hormone-dependent tumours. The present invention prepares analogues of human GnRH (hGnRH) and Lamprey GnRH-III showing antitumour effect in human tumour cell cultures. This aim was solved by the preparation of peptides of general formula (IV) as well as their pharmaceutically acceptable salts and esters.

The invention is based on the recognition that these compounds exert a direct antitumour action against human tumour cells. Unexpectedly, compounds containing only natural L-amino acids also show a direct antitumour effect. Namely, antitumour GnRH analogues known at present contain at least one of non-natural D-amino acids in the case of agonists and usually several non-natural D-amino acids in the case of antagonists.

Furthermore, it has been recognized that for more amino acid groups of antitumour GnRH analogues Lys groups may be substituted without any decrease in the favourable antitumour effect of the molecule. This is advantageous since, through the e-amino group of Lys, the peptide can be connected to suitably selected larger molecules containing an acylating group. In this case, the macromolecules may be carrier molecules of the peptide and can thereby promote the maintenance of a steady, high level of the GnRH analogue in the body.

The invention relates to the peptides of general formula (IV), $$X\text{-}R^1\text{-}R^2\text{-}R^3\text{-}R^4\text{-}R^5\text{-}R^6\text{-}R^7\text{-}R^8\text{-}Pro\text{-}R^{10}\text{-}Y \qquad (IV)$$

wherein

X means hydrogen, acetyl group or propionyl group when $R^1$ is different from pGlu; or an intramolecular acid amide bond when $R^1$ stands for pGlu;

$R^1$ stands for pGlu, Glu, D-Trp, D-Cpa, D-Nal or D-Phe;

$R^2$ means His, D-Phe or D-Cpa;

$R^3$ represents D-Cpa, D-Pal or L- or D-Trp optionally protected on the indolyl moiety;

$R^4$ stands for Ser; or Lys optionally protected on the ε-amino group;

$R^5$ means Tyr; or Lys optionally protected on the ε-amino group; or His;

$R^6$ stands for Asp, Glu, D-Lys and optionally ε-amino methylated derivatives thereof; as well as D-Trp, D-Phe, D-Leu, D-Ala, D-Cpa or D-Arg;

$R^7$ represents Phe, Leu or N-Me-Leu; or L-Trp optionally protected on the indolyl moiety;

$R^8$ means Lys optionally protected on the ε-amino group; Arg, Gln; or $R^6$ and $R^8$ together can form an intramolecular ring through the ε-amino group of Lys when $R^6$ is Asp and $R^8$ means Lys;

$R^{10}$ stands for Gly, D-Ala or a valence bond; and

Y represents OH or $NH_2$ group when $R^{10}$ means Gly or D-Ala; or an ethylamide group when $R^{10}$ means a valence bond, as well as the pharmaceutically acceptable salts and/or esters of these compounds. The invention furthermore relates to pharmaceutical compositions containing the peptide of general formula (IV) and/or pharmaceutically acceptable salts and/or esters thereof.

The abbreviations used in the description agree with the nomenclature accepted in the peptide chemistry and published in Edsall et al., eds., J. Biol. Chem. 241, 527–533 (1966); Tabor et al., eds., J. Biol. Chem. 247, 977–983 (1972); furthermore, D-Nal stands for β-(2-naphthyl)-D-alanine, D-Cpa means p-chlorophenyl-D-alanine and D-Pal stands for β-(3-pyridyl)-D-alanine. When not noted otherwise, all amino acids named in the description are in L-configuration.

In the peptides according to the invention the preferred protective group of the indolyl moiety of Trp is For; the preferred protective group of the C-amino group of Lys is Fmoc. The pharmaceutically acceptable salts of the peptides of general formula (IV) are acid-addition salts formed with pharmaceutically acceptable organic or inorganic acids, e.g. acetates or hydrochlorides.

The compounds of general formula (IV) can be prepared in liquid phase by using methods known in the peptide chemistry (by condensations carried out in the defined sequence of suitably protected amino acids or fragments prepared therefrom) or in a particularly preferable way—by using the solid-phase peptide synthesis. A peptide obtained in the form of its salt can be convened to an other salt in a known manner. If desired, the ester groups of ester compounds obtained may be cleaved.

The peptide of general formula (IV) may be administered mainly in the form of injectable solutions, infusions or intranasal compositions. Being decomposed in the digestive system, they cannot be administered orally in themselves but may be administered in any other route. The injections may be given in intramuscular, intravenous or subcutaneous route.

The active agents of general formula (IV) can be formulated to pharmaceutical compositions by using known methods of the pharmaceutical techniques. The active agent can be transformed also to compositions with prolonged action (e.g. in the form of microcapsules or microgranules) in the usual way. In addition to the active agent, auxiliaries commonly used in the pharmaceutical industry such as a liquid vehicle useful for injection purposes (isotonic saline or phosphate buffer solution) may be used. If necessary, the compositions may contain stabilizers (e.g. ascorbic acid), too.

The preparation of peptides according to the invention is illustrated by the following Examples. The chemical purity and identification of both intermediary and final products were controlled by using thin-layer chromatography (TLC); those of the final products were examined by means of HPLC too. The thin-layer chromatography values were determined on Kieselgel sheets (DC Alufolien, Merck) by using the following solvent mixtures:

1. Ethyl acetate/pyridine/water/acetic acid 15:20:6:11
2. Ethyl acetate/pyridine/water/acetic acid 30:20:6:11
3. Ethyl acetate/pyridine/water/acetic acid 60:20:6:11
4. Ethyl acetate/pyridine/water/acetic acid 120:20:6:11
5. Ethyl acetate/pyridine/water/acetic acid 240:20:6:11
6. n-Butanol/acetic acid/water 4:1:1
7. n-Butanol/acetic acid/water 4:1:2

The side chains of protected amino acids are protected by a benzyl group in the case of Tyr and Ser; by a (benzyloxy) carbonyl (Z) group or a 9-fluorenyl(methoxycarbonyl) (Fmoc) group for preparing an intermediary peptide analogue in the case of Lys; by a tosyl (Tos) group in the case of Arg and His; and by a cyclohexyl (Chx) group in the case of carboxy groups of Asp and Glu.

The invention is illustrated in more detail by description of the preparation process of the preferred analogues listed hereinbelow:

1. [Lys($\epsilon$-Fmoc)]$^5$-GnRH-III,
2. Lys$^5$-GnRH-III,
3. Lys$^5$,cyclo[Asp$^6$-Lys$^8$]-GnRH-III,
4. Lys$^5$,[Lys($\epsilon$-Fmoc)]$^8$-GnRH-III,
5. Lys$^4$,[Lys($\epsilon$-Fmoc)]$^8$-GnRH-III,
6. Lys$^4$-GnRH-III,
7. [Lys($\epsilon$-Ac)]$^4$-GnRH-III,
8. Glu$^6$-GnRH-III,
9. cyclo[Asp$^6$-Lys$^8$]-GnRH-III,
10. D-Ala$^{10}$-GnRH-III,
11. H-D-Trp$^1$, [Lys($\epsilon$-Fmoc)]$^8$, D-Ala$^{10}$-GnRH-III,
12. Ac-D-Trp$^1$, D-Ala$^{10}$-GnRH-III,
13. H-D-Trp$^1$, D-Ala$^{10}$-GnRH-III,
14. [Trp(For-Ind)]$^{3,7}$-GnRH-III,
15. Phe$^7$-GnRH-III,
16. GnRH-III(1-9)-ethylamide,
17. Lys$^5$, D-Trp$^6$-hGnRH,
18. Lys$^4$, D-Trp$^6$-hGnRH,
19. H-Glu$^1$, D-Trp-hGnRH,
20. Lys$^5$, D-Phe$^6$-hGnRH(1-9)-ethylamide,
21. Lys$^4$, D-Phe$^6$-hGnRH(1-9)-ethylamide,
22. Lys$^5$, D-Cpa$^6$-hGnRH(1-9)-ethylamide.

On investigating the capacity factor of some analogues of high importance by using HPLC the following results were obtained:

| Analogue Example No. | k' | Methanol % |
|---|---|---|
| 3 | 3.57 | 38 |
| 5 | 9.28 | 55 |
| 6 | 3.57 | 30 |
| 7 | 11.57 | 30 |
| 8 | 7.57 | 30 |
| 17 | 9.57 | 38 |
| 19 | 14.10 | 38 |
| 19 | 8.71 | 40 |

ISCO model 2350 pump 1 ml/min, ISCO V4 detector (215 nm). Column: BST, ODS Hypersil 5 $\mu$m, 270×4 mm. Eluent: MeOH/0.1 M NaH$_2$PO$_4$ (pH=2.22).

$$k' = \frac{T_R - t_0}{t_0}$$

Other and further aspects, features, and advantages of the present invention will be apparent from the following description of the presently preferred embodiments of the invention given for the purpose of disclosure.

DETAILED DESCRIPTION OF THE INVENTION

The abbreviations used in the description agree with the nomenclature accepted in the peptide chemistry and published in Edsall et al., eds., J. Biol. Chem. 241, 527–533 (1966); and Tabor et al., eds., J. Biol. Chem. 247, 977–983 (1972); furthermore, D-Nal stands for a-(2-naphthyl)-D-5-alanine, D-Cpa means p-chlorophenyl-D-alanine and D-Pal stands for a-(3-pyridyl)-D-alanine. When not noted otherwise, each of the amino acids mentioned in the description is in L-configuration.

The new compounds of general formula (I) can be prepared by coupling pharmacologically active polypeptides, preferably GnRH analogues, to molecules of general formula (Ia) in the following way: a) pharmacologically active compounds containing a free amino group are coupled to N-vinylpyrrolidone/maleic anhydride copolymer of general formula (Ib)

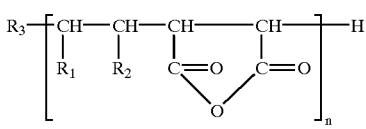

(Ib)

known per se but not used in the therapy up to the present, wherein $R_1$ $R_2$ and $R_3$ are as defined for the general formula (Ia); b) a compound of general formula (Ib) is reacted with an activated ester of general formula (IR)

H-X-OQ     (III)

of an amino acid or an oligopeptide, then the pharmacologically active polypeptides are coupled to the carrier compound of general formula (Ic) obtained by means of the activated ester groups. The compounds obtained can be transformed to salts of a pH value of 7.2, preferably to sodium salts.

The pharmacologically active molecule (A) appearing in the general formula (I) is preferably an agonistic or antagonistic GnRH analogue. The X group of compounds of general formula (I) means an amino acid group or an oligopeptide group of at most six members built up from native or non-natural amino acids. These can be prepared by using processes known in the peptide chemistry.

The invention is based on the following recognitions:

1. In comparison to the corresponding pharmacologically active peptide hormones, chiefly GnRH analogues, in relation to the original effect of the peptide hormone molecules, the compounds of general formula (I) show an increased action prolonged in time.

2. Compounds of general formula (I) containing a spacer group as X, i.e. wherein r is different from 0, show an even more favourable effect than those compounds containing no X group. Simultaneously, no toxic side effects are shown by the compounds containing X group or those without X group; and these compounds retain all effects of the pharmacologically active polypeptide molecule A.

3. Compounds of general formula (I) and their salts, wherein A represents a GnRH analogue of formula (IIa) coupled through the amino group of the side chain of the Lys group of the peptide hormone, Y, W, V, X, r, k, z and u are as defined for the general formula (I), are tumour-inhibiting compounds retaining and even exceeding the known pharmacological effects of the analogue (Ha), i.e. pGlu-His-Trp-Ser-His-Asp-Trp-Lys-Pro-Gly-NH$_2$ (SEQ ID NO:3); MI-1544: Ac-D-Trp$^{1,3}$,D-Cpa$^2$,D-Lys$^6$,D-Ala$^{10}$; thus, they inhibit the growth of both steroid-dependent and steroid-independent tumours. In addition, they induce a reversible chemical castration enhancing the antitumour action in the case of steroid-dependent tumours.

4. Compounds of general formula (I), wherein A stands for a GnRH antagonist analogue of formula (IIb), i.e., MI-1892: Ac-D-Trp$^{1,3}$,D-Cpa$^2$,Lys$^5$, [Asp(a-DEA)]$^6$,D-Ala$^{10}$-Gln$^8$-GnRH coupled through the n-amino group of lysine in position 5, and Y, W, V, X, r, k, z as well as u are as defined for the general formula (I), are selective tumour-inhibiting agents according to their antagonistic character; thus, they inhibit the growth of both steroid-dependent and steroid-independent tumours, actually to a degree surpassing the effect of the compound of formula (IIb). Both the antagonist of formula (IIb) and its derivative of general formula (I) possess an irreversible chemical castration effect which, together with the selective direct tumour-inhibiting effect, is preferred from the view-point of effectivity of tumour inhibition. It has unexpectedly been observed that the antagonist of formula (IIb) possesses also an effect stimulating the immune system, and this effect is retained by the derivative of general formula (I), too. This recognition is surprising, since the therapeutic use of tumour-inhibiting GnRH antagonists known up to now has been impeded just by their immunosuppressive action.

5. Compounds of general formula (I), wherein A stands for the lamprey GnRH-III coupled through the n-amino group of the lysine moiety in position 8, whereas Y, W, V, X, r, k, z and u are as defined for the general formula (I), are selective tumour-inhibiting agents under in vivo conditions and therefore, they inhibit the growth of both steroid-dependent and steroid-independent tumours in spite of the fact that the GnRH-III alone shows only a negligible in vivo effect. Conjugates of general formula (I) of GnRH-III, exceeding the effects of sustained-release hGnRH compositions, resulted in a tumour-free state of the experimental animals in a treatment period, where only a decrease in the tumour growth was observed by using known compositions. The most preferable compounds of general formula (I) according to the invention were prepared by conjugating the following GnRH analogues of formulae (IIa) to (IIi): human GnRH (hereinafter GnRH):

pGlu-His-Trp-Ser-Tyr-Gly-Leu-Arg-Pro-Gly-NH$_2$ (SEQ ID NO:4); chicken GnRH (hereinafter Gln$^8$-GnRH):

pGlu-His-Trp-Ser-His-Asp-Trp-Lys-Pro-Gly-NH$_2$ (SEQ ID NO:2); lamprey GnRH-III (hereinafter GnRH-III):

pGlu-His-Trp-Ser-His-Asp-Trp-Lys-Pro-Gly-NH$_2$ (SEQ ID NO:3); MI-1544: Ac-D-Trp$^{1,3}$,D-Cpa$^2$,D-Lys$^6$,D-Ala$^{10}$-GnRH antagonist analogue of formula (IIa) of human GnRH;

MI-1892: Ac-D-Trp$^{1,3}$,D-Cpa$^2$,Lys$^5$,[Asp(a-DEA)]$^6$,D-Ala$^{10}$-Gln$^8$-GnRH; antagonist analogue of formula (IIb) of chicken GnRH;

SJ-1004: D-Phe$^2$,D-Trp$^3$,D-Lys$^6$-GnRH; antagonist analogue of formula (IId) of human GnRH;

TH-614: Lys$^5$,cyclo(Asp$^6$-Lys$^8$)-GnRH-III; analogue of formula (IIe) of lamprey GnRH-III;

HB-694: Lys$^4$,[Lys(n-Fmoc)]$^8$-GnRH-III; analogue of formula (IIf) of lamprey GnRH-III;

TH-602: Lamprey GnRH-III; see above the formula; GnRH of formula (IIc);

HB-685: Lys$^4$-GnRH-III; analogue of formula (IIg) of lamprey GnRH-III;

TH-609: D-Lys$^6$-GnRH; analogue of formula (IIh) of human GnRH;

TH-615: Lys$^5$,D-Trp$^6$-GnRH; analogue of formula (IIi) of human GnRH.

The GnRH analogues were coupled either directly or through an X group, i.e. spacer moiety, to the polymer designated as P. For naming the spacers, the one-letter marking of the amino acids are used, e.g. H-GFLG-OH: H-Gly-Phe-Leu-Gly-OH (SEQ ID NO:5) (peptide in the form of its sodium salt); P: polyvinylpyrrolidone/maleic acid copolymer sodium salt, i.e. a salt of formula (Id), wherein one of $R_1$ and $R_2$ means hydrogen whereas the other one is a group (B), n is 66, transformed to the sodium salt by n equivalents of NaHCO$_3$.

The biological study of the following substances was carried out: P-GLG-1892: compound of general formula (I), wherein A=(IIb) group coupled to the Y=(Ia) group through X=−GLG-moiety; n=66, r=0.1n, k=0.3r, z=0, u=1.9n and W=OH or ONa, respectively, pH=7.2;

P-GFLG-1544: compound of general formula (1), wherein A=(IIa) group coupled to the Y=(Ia) group through the X=–GFLG-moiety; n=66, r=0.1n, k=0.3r, z=0, u=1.9n and W=OH or ONa, respectively, pH 7.2;

P-1892: compound of general formula (I), wherein A=(IIb) group, n=66, r=0, k=0.024n, z=0, u=1.9n, W=OH or ONa, respectively, pH 7.2;

P-GFLG-1892: compound of general formula (I), wherein A=(IIb) group coupled to the Y=(Ia) group through an X=–GFLG-moiety; n=66, r=0.1n, k=0.3r, z=0, u=1.9n and W=OH or ONa, respectively, pH 7.2;

P-GFLG-609: compound of general formula (I), wherein A=(IIb) group, coupled to the Y=(Ia) group through an 20 X=–GFLG-moiety; n=66, r=0.1n, k=0.3r; z=0; u=1.9n and W=OH or ONa, respectively, pH=7.2;

P-GFLG-1004: compound of general formula (I), wherein A=(IId) group, coupled to the Y=(Ia) group through an 25 X=–GFLG-moiety; n=66, r=0.1n, k=0.3r; z=0; u=1.9n and W=OH or ONa, respectively, pH 7.2;

P-GFLG-614: compound of general formula (I), wherein A=(IIe) group, coupled to the Y=(Ia) group through an X=–GFLG-moiety; n=66, r=0.1n, k=0.3r; z=0; u=1.9n and W=OH or ONa, respectively, pH=7.2;

P-GFLG-685: compound of general formula (I), wherein A=(IIg) group, coupled to the Y=(Ia) group through an X=–GFLG-moiety; n=66, r=0.1n, k=0.3r; z=0; u=1.9n and W=OH or ONa, respectively, pH=7.2;

P-GFLG-602: compound of general formula (I), wherein A=(GnRH-III) group, coupled to the Y=(Ia) group through an X=–GFLG-moiety; n=66, r=0.1n, k=0.3r; z=0; u=1.9n and W=OH or ONa, respectively, pH 7.2;

P-GFLG-615: compound of general formula (I), wherein A=(IIi) group, coupled to the Y=(Ia) group through an X=–GFLG-moiety; n=66, r=0.1n, k=0.3r; z=0; u=1.9n and W=OH or ONa, respectively, pH=7.2;

P-FLG-892: compound of general formula (I), wherein A=(IIb) group, coupled to the Y=(Ia) group through an X=–GFLG-moiety; n=66, r=0.1n, k=0.3r; z=0; u=1.9n and W=OH or ONa, respectively, pH=7.2;

P-Ahx-1892: compound of general formula (I), wherein A=(IIb) group, coupled to the Y=(Ia) group through an X=–Ahx-moiety; n=66, r=0.1n, k=0.3r; z=0; u=1.9n and W=OH or ONa, respectively, pH 7.2.

The biological tests were carried out by using the materials and methods following hereinafter. Certain human mammary carcinoma cell lines or xenografts prepared therefrom are useful for the biological testing of the conjugates.

Human cell lines used in in vitro experiments. MCF-7 human mammary tumour cell line was stabilized in 1973 by Soule et al. [J. National Cancer Inst., 51, 1409–1416] from the pleural fluid of mammary carcinoma patients. The cells grow in monolayer and are epithelial in their character. MDA-MB-231 human mammary carcinoma cell line was isolated and stabilized in 1974 by Cailleau et al. [J. National Cancer Inst., 53, 661–674] similarly from pleural fluid. These cells also grow in monolayer. PC3 human prostate carcinoma cell line was stabilized 20 in 1979 in cell culture by Kaighn et al. [Investigative Urology, 17, 16–23]; the cells are of simple epithelium type and form compact colonies in clonogenic assays. Ishikawa cell line originated from adenocarcinoma of human endometrium [Nishida et al.: Obstet. Gynecol. Jpn, 37 1103–1111 (1985)], has epithelial character and contains steroid as well as GnRH receptors. Human tumour cell lines are maintained in plastic flasks (Greiner) in Dulbecco-modified Eagle-MEM (DMEM GIBCO) nutritive medium. The medium used herein contained 10% of fetal calf serum (FCS).

The MCF-7 cell line is estradiol-receptor (ER) positive and GnRH receptor-positive. Therefore, it is suitable to study the receptor-mediated direct effect of GnRH; being an in vivo model system, it is useful for investigating both the direct and indirect effects of GnRH. Being an ER-negative and GnRH receptor-positive in vitro and in vivo model system, MDA-MB-231 cell line is useful to study the direct effect of GnRH. Based on literature data, PC3 human prostate carcinoma cell line contains receptors specifically binding GnRH, whereby the essential condition for the direct effect is fulfilled. Ishikawa cell line is originated from human endometrium adenocarcinoma, contains ER and PgR proteins and is GnRH receptor-positive. Thus, it is useful for investigating the direct effect of GnRH. Buserelin, chemically [D-Ser(tBu)]$^6$,desGly$^{10}$-hGnRH(1-9)EA, is a tumour-inhibiting agonist being used in a retard form in clinical practice; conclusively, the substance itself but not its retard form was employed in the in vitro experiments.

The preparation of the known polymeric carrier and the investigation of compounds of general formula (I) as well as of the spacers of general formula X were carried out as follows.

NVP-MA samples used herein were prepared according to the literature [Reddy et al.: Polymer 25, 115–120 (1984)]. Activated esters of oligopeptides employed as spacers were preferably nitrophenyl esters obtained by using classic methods of peptide chemistry. The coupling of peptides to polymers can be accomplished in solvents, such as dimethylsulfoxide (DMSO), dimethylformamide (DMF) or dimethylacetamide. DMF was used as solvent.

Nitrophenyl esters of peptides were characterized by amino acid analysis. The retention factors referred to were determined on Kieselgel 60 F254 thin layer by using the following developing systems:

1. pyridine:acetic acid:water:ethyl acetate 20:6:12:62;
2. chloroform:methanol:water 10:5:1.

High pressure liquid chromatography (HPLC) examinations were carried out on a C-18 reverse-phase column at a flow rate of 0.5 ml/min by using the following gradients:

Eluent A: 5% of acetonitrile plus 95% of triethylamine-phosphate buffer of pH 2.25;

Eluent B: 80% of acetonitrile plus 20% of triethylamine-phosphate buffer of pH 2.25; 100% of eluent A up to the 5th minute; to 60% of eluent A up to the 10th minute; to 35% of eluent A up to the 30th 25 minute; to 0% of eluent A up to the 35th minute; 0% of eluent A up to the 40th minute; and to 100% of eluent A up to the 45th minute. The detection was performed at 280 nm with an UV detector. The conjugates were purified by ultrafiltration on AMICON PM10 membrane.

The results advantages of the new compounds can be summarized as follows. Based on the in vitro examinations it can be stated that the proliferation- and colony formation-inhibiting effects of the conjugates P-GFLG-1544 and P-GFLG-1892—containing the GFLG tetrapeptide spacer group—highly exceed the antitumour effect of both the GnRH analogue substances (i.e. MI-1544 or MI-1892) as well as that of the spacer-containing carrier (P-GFLG-OH) and even that of the compound P-1892. The conjugates (i.e. compounds built up from the carrier and GnRH analogue) resulted in colony formation-inhibition of 100% above a concentration of 20 μM. Such a high grade of inhibition could until now be achieved only by the use of cytostatics. Based on the results both the polymeric starting substance and the spacer-containing polymer as a polyanion in themselves also exert a direct antitumour effect, and, when coupled covalently to GnRH antagonists, they enhance the direct antitumour action of the antagonists.

According to the in vivo studies the conjugates P-GFLG-1544 and P-GFLG-1892 as well as the carrier P-GFLG-OH proved to be non-toxic. The conjugates P-GFLG-1544 and P-GFLG-1892 resulted in a tumour volume diminution of 30 to 35% in the second week and 37 to 49% in the fourth week of treatment on the ER-positive, GnRH receptor-positive MCF-7 human mammary carcinoma xenograft; whereas a tumour volume diminution of 37 to 42% could be observed on the ER-negative, GnRH receptor-positive MDA-MB-231 human mammary carcinoma xenograft. This result is considered to be significant since the degree of tumour inhibition observed by us on human carcinoma xenograft is nearly identical with that of the sustained-release composition of SB-75, a GnRH antagonist [Szepeshazi et al.: Breast Cancer Res. Treat. 21, 181–192 (1992)], which had been achieved on the MXT mouse mammary carcinoma which is more sensitive.

The substance MI-1892 and its conjugate P-GFLG-1892 possess a direct, selective tumour-inhibiting effect. Namely, in contrast to substance MI-1544 and its conjugate P-GFLG-1544, they exert a minimum chemical castration effect. Based on this fact it can be supposed that they act on a broader spectrum of mammary carcinomas and therefore, on hormone-(estrogen-)-independent tumours, too.

When investigating the effect of the compounds on the cellular and humoral immune system it was stated that MI-1892 as selective chicken GnRH antagonist as well as the conjugate P-GFLG-1892 containing the antagonist and the spacer-containing P-GFLG, a novel polyanionic macromolecule, increased the activity of T-lymphocytes against bovine red blood cell (BRBC) antigen (by using the method of rosette formation). On the basis of examinations of the antibody production of B-lymphocytes, MI-1892 and P-GFLG-OH as well as the conjugate P-GFLG-1892 containing MI-1892 moiety strengthened the humoral immune response, too.

The immunosuppressive side effect of cytostatics used in tumour therapy is commonly known. This effect can be compensated to a certain grade by various immunostimulants (endotoxin, levamisole). Polypeptides with much lower molecular weights (about 40,000 to 80,000) are also capable of protecting against immunosuppressive effect [Ga ál et al.: J. Biol. Resp. Modif. 5, 148–159 (1986)]. The molecular weight of the novel polyanionic P-GFLG-OH macromolecule tested by us is about 10,000, that of MI-1892 is about 2000, i.e. relatively low; therefore, their immunostimulatory activity was unexpected. The importance of these results is reflected by the fact that MI-1892 administered to mice in a dose of 50 $\mu$g/mouse or 100 $\mu$g/mouse, respectively, increased the humoral immune response to more than twofold or threefold, respectively; the increase was twofold in the case of P-GFLG-OH. The conjugate P-GFLG-1892 also possesses an immunostimulatory effect. The investigation of the cellular immune response showed that MI-1892 given in a dose of 100 $\mu$g/mouse increased the response to nearly twofold; this increase was twofold in the case of P-GFLG-OH and P-GFLG-1892.

The novel polycarboxylic acid derivatives according to the invention are very preferable carriers for peptide hormones since they can be prepared with a good reproducibility and with a low polydispersity in the aimed range of molecular weights and they are water-soluble.

Known polycarboxylic acid derivatives also possess a weak tumour-inhibiting action and can similarly favourably be used as carrier compounds. By coupling pharmacologically active compounds such as GnRH analogues to the polymers of the invention, novel compounds are obtained which exert an increased therapeutic efficiency in comparison to that of their structural moieties.

The new conjugate P-GFLG-1544 is a compound with favourable therapeutic effect for the following reasons: It has a selective tumour-inhibiting effect proved by the direct inhibition of cell proliferation. Thus, it inhibits not only the growth of steroid-dependent but also that of steroid-independent tumours as demonstrated by investigations carried out on MDA-MB-231 mammary tumour cells. Due to the antagonistic effect, the coupled MI-1544 possesses a reversible castration effect. This effect is proved by the change of uterus weight measured during in vivo treatments as well as the decrease in the cytosolic progesterone receptor (cPgR) level of uterus. A very important advantage of this effect is that the hormone status is re-established by suspending the treatment. This is opposed to the chirurgical intervention and irradiation, which are irreversible and refused by many patients. The advantage of castration effect is that in the case of steroid-dependent tumours the selective direct and castration effects are summarized to result in a stronger inhibition of the tumours.

The castration effect is illustrated by the following data. After a treatment for four weeks the uterus weights of animals bearing MCF-7 xenografts were decreased by 42% (control=0.1980 q 0.0120 g; P-GFLG-1544=0.1149+0.0110 g); after a treatment for twelve weeks the uterus weights of animals bearing MDA-MB-231 xenografts were decreased by 50% (control=0.0263+0.0028 g, P-GFLG-1544=0.0133 q 0.0018 g). The weight of uterus was not decreased but slightly increased by P-GFLG-OHalone (0.0337 q 0.0034 g, 128%). The change of progesterone level was proved by the significant decrease (of 54%) of the uterus cPgR level of animals bearing MCF-7 xenografts (control=517 q 45 femtomol/mg of protein, P-GFLG-1544=241 q 28 femtomol/mg of protein).

In opposition to several known GnRH antagonists, P-GFLG-1544 does not possess immunosuppressive effect. Summing up: the conjugate P-GFLG-1544 not only retained but also substantially exceeded both the selective tumour-inhibiting as well as the castration effects of the MI-1544, an antagonist analogue of GnRH, mainly in respect of tumour inhibition. No adverse side effects have been observed during the investigations on the conjugate. Due to its prolonged effect this novel antagonist compound can be utilized for in vivo tumour inhibition. The new conjugate P-GFLG-1892 is a favourable compound with therapeutic effect for the following reasons: It has a selective tumour-inhibiting effect. Therefore, it inhibits the growth of both steroid-dependent and steroid-independent tumours, which was proved by investigations on MDA-MB-231 cells.

The GnRH antagonist MI-1892 and the conjugate containing the antagonist possess a weaker castration effect in comparison to MI-1544 and its conjugate. The castration effect of the conjugate was demonstrated by the change in uterus weight measured during in vivo treatments as well as by the decrease in the cytosolic progesterone receptor (cPgR) level of uterus. After a treatment for four weeks the uterus weight of animals bearing xenograft was decreased by 39% (control 0.1980 q 0.0120 g, P-GFLG-1892=0.1215 q 0.0130 g). After a treatment for twelve weeks the uterus weight of animals bearing MDA-MB-231 was decreased by 20% (control=0.0263 q 0.0028 g, P-GFLG-1892=0.0215 q 0.0017 g). The weight of uterus was not decreased but slightly increased by P-GFLG-OH alone (0.0337 q 0.0034 g, 128%). The change in the progesterone level was proved by the 23% decrease in the uterus cPgR level of animals bearing MCF-7 xenograft (control=517 q 45 femtomol/mg of protein, P-GFLG-1892=376 q 33 femtomol/mg of protein).

In opposition to several known GnRH antagonists, it has no immuno-suppressive effect. It is a new recognition that this novel GnRH antagonist analogue and the conjugate containing this analogue possess immunostimulatory effect as proved by the humoral and cellular immune response investigations.

On comparison to healthy individuals, the functioning of the protective mechanism (immunostatus) of patients suffering from tumour is more unfavourable. Since the protective (immune) mechanism is enhanced by the compound, its tumour-inhibiting action can more strongly become valid. The novel conjugate P-GFLG-GnRH-III is a compound possessing favourable therapeutic action for the following reasons: It has a selective tumour-inhibiting effect.Therefore, it inhibits the growth of both the steroid-dependent and steroid-independent tumours which was proved by investigations on MDA-MB-231 cells. It has no castration effect since the cycle of female rats is not influenced even by a high dose of the coupled GnRH-III during three cycles observed. This effect may particularly be preferred on young patients suffering from mammary tumour, where a castration would cause psychic disturbances. In a way different from other conjugates, P-GFLG-GnRH-III gradually induces an inhibition of continually increasing grade during the long-lasting treatment for 7 weeks; and at the end of treatment, tumour-free animals are observed whereas in the case of other conjugates the degree of inhibition increases only up to the fifth week of treatment, then a stagnation in the grade of inhibition can be observed.

The pharmaceutical compositions containing the compound of general formula (I) according to the invention may be prepared by transforming the compound of general formula (I) or a pharmaceutically acceptable salt or complex thereof to a composition with carriers and/or additives commonly used in the pharmaceutical industry by using known operations of the pharmaceutical techniques.

The pharmaceutical composition for therapeutic use may contain any filling material and carrier used in the therapy (e.g. calcium carbonate, talc); solvent (such as water, an aqueous solution containing ethanol and/or polyalcohol, e.g. polyethylene glycol and/or glycerol and the like); salts (e.g. sodium chloride for adjusting the physiological osmotic pressure; or e.g. chlorides of iron, cobalt, zinc or copper and the like for supplementing trace elements); solubilizing additives, e.g. complex-forming agents (cyclodextrins, crown ethers, native proteins, saponins and the like); compounds diminishing the relative permittivity of the solvent such as ethanol, polyols (polyethylene glycol or glycerol); tablet-disintegrating agents; complex-forming agents commonly used in sustained-release compositions (e.g. water-insoluble cyclodextrin derivatives, native and artificial polymers, crown ethers and the like); pH-adjusting compounds such as mineral and organic buffers; taste-improving agents (beet-sugar, fructose and dextrose, saccharins, inverted sugar and the like); antioxidants (e.g. vitamin C); as well as other active ingredients promoting the effectuation of the action of active agents of general formula (I). The pharmaceutical compositions may be oral such as tablets, pills, drages, hard or soft capsules, microcapsules, solutions, emulsions or suspensions; or parenteral, e.g. injectable solutions, slow and rapid infusions; as well as pharmaceutical compositions useful for rectal administration such as suppositories; furthermore creams or jellies. There also exists the possibility of incorporating to liposomes the pharmaceutical compositions developed for the above uses. The bioconjugates of general formula (I) can be utilized also in aerosol compositions targeted at the absorption through the skin surface or the lungs, respectively. For the preparation of tablets, drages or hard gel capsules, e.g. calcium carbonate, talc, fats, waxes or polyalcohols, having an appropriate density, are useful carriers.

For the preparation of solutions and syrups, e.g. water, polyalcohols (e.g. polyethylene glycol or glycerol), beet-sugar or dextrose may be used as carriers. Parenteral compositions may contain water, alcohol, polyalcohols or vegetable oils as carriers. Carriers of suppositories may be e.g. oils, waxes, fats or polyalcohols having a suitable density. The bioconjugates of general formula (I) are useful for therapeutic utilization in combination with artificial and native active agents, too. The bioconjugates of general formula (I) are effective in a dose range of 0.01 to 100 $\mu$g/kg in subcutaneous, intramuscular or intravenous injections. The dose to be used in the practice is dependent on the type of disease as well as on the state and age of the patient and it should be determined by the physician.

The invention is further illustrated by the following non-limiting Examples, wherein the term "active substance" relates to the GnRH analogue moiety of the conjugates. The following examples are given for the purpose of illustrating various embodiments of the invention and are not meant to limit the present invention in any fashion.

EXAMPLE 1

Preparation of Poly(N-vinylpyrrolidone-co-maleic Acid)-Gly-Phe-Leu-Gly (SEQ ID NO:5) Nitrophenyl Ester After dissolving poly(N-vinylpyrrrolidone-co-maleic anhydride) [average molecular weight: 10,000, IR: 1840 $cm^{-1}$, 1790 $cm^{-1}$ (anhydride), 1660 $cm^{-1}$ (NCO of pyrrolidone)] in anhydrous dimethyl formamide 10 mol% of H-Gly-Phe-Leu-Gly (SEQ ID NO:5) nitrophenyl ester trifluoroacetate ($R_{f1}$: 0.50) and an equivalent amount of triethylamine were added. After 3 hours the product was precipitated by adding diethyl ether, filtered and thoroughly washed with ether. The presence of nitrophenyl ester content in the product obtained was proved by IR spectroscopy (1840 $cm^{-1}$, 1790 $cm^{-1}$ anhydride, 1740 $cm^{-1}$ COOH, 1660 $cm^{-1}$ NCO, 1540 $cm^{-1}$, 1350 $cm^{-1}$ $NO_2$) and determined by its ultraviolet absorption measured at 400 nm in sodium 10 hydrogen carbonate solution (molar extinction coefficient: 1660). By ultrafiltration of an aliquot part it was controlled that the product was free from unbound peptide nitrophenyl ester. After dissolving the polymer in absolute DMF a calculated amount (2 equivalents) of water was added for hydrolyzing the anhydride groups. The termination of hydrolysis was determined by the IR spectrum of a sample (IR: 1740 $cm^{-1}$ COOH, 1540 $cm^{-1}$, 1350 $cm^{-1}$ $NO_2$).

EXAMPLE 2

Preparation of Poly(N-vinylpyrrolidone-co-maleic Acid)-Phe-Leu-Gly Nitrophenyl Ester The product was prepared and characterized as described in Example 1 by coupling H-Phe-Leu-Gly nitrophenyl ester hydrochloride ($R_{f1}$: 0.59) (IR: 1740 $cm^{-1}$ COOH, 1540 $cm^{-1}$, 1350 $cm^{-1}$ $NO_2$).

EXAMPLE 3

Preparation of Poly(N-vinylpyrrolidone-co-maleic Acid)-Gly-Leu-Gly Nitrophenyl Ester The product was prepared and characterized as described in Example 1 by coupling H-Gly-Leu-Gly nitrophenyl ester trifluoroacetate ($R_{f2}$: 0.53). (IR: 1740 cm$^{-1}$ COOH, 1540 cm$^{-1}$; 1350 cm$^{-1}$ NO$_2$).

EXAMPLE 4

Preparation of Poly(N-vinylpyrrolidone-co-maleic Acid)-Ahx Nitrophenyl Ester

The product was prepared and characterized as described in Example 1 by coupling H-Ahx nitrophenyl ester acetate ($R_{f1}$: 0.7). (IR: 1740 cm$^{-1}$ COOH, 1540 cm$^{-1}$, 1350 cm$^{-1}$ NO$_2$).

EXAMPLE 5

Preparation of Ac-D-Trp$^{1,3}$,D-Cpa$^2$,{Lys[n-poly(N-vinylpyrrolidone-co-maleic Acid)-Gly-Phe-Leu-Gly-(SEQ ID NO:5)]}$^5$,[a-Asp(DEA)]$^6$, D-Ala$^{10}$-GnRH (Abbreviated: P-GFLG-1892)

After adding 1 equivalent of MI-1892 (calculated for the nitrophenyl ester groups) to the solution prepared according to Example 1, the pH of the solution was adjusted between 7 and 8 by adding triethylamine. After 24 hours the reaction mixture was diluted to its 20-fold volume by adding water and an 5% NaHCO$_3$ solution was added for the complete hydrolysis of the unreacted nitrophenyl ester groups. Low molecular materials were removed by ultrafiltration and the high molecular fraction was lyophilized. The purity of the product was controlled by HPLC (Rt: 34.48 min, the retention time of MI-1892 is 20.61 min) and the active ingredient content was determined by UV spectrophotometry in the range of 200 to 450 nm (the specific extinction of MI-1892 is 10,400 at 280 nm). Simultaneously, it was stated that the product did not contain any free or unbound nitrophenol (between 380 and 420 nm).

EXAMPLE 6

Preparation of Ac-D-Trp$^{1,3}$,D-Cpa$^2$,{D-Lys[n-Poly-(N-vinylpyrrolidone-co-maleic Acid)-Gly-Phe-Leu-Gly (SEQ ID NO:5)]}$^6$,D-Ala$^{10}$-GnRH (Abbreviated: P-GFLG-1544)

Example 5 was followed, except that MI-1544 was used as GnRH analogue. The purity of the product was controlled by HPLC [retention time (Rt): 29.96 min, that Rt of MI-1544 is 22.93 min], its active ingredient content was determined by 10 UV spectrophotometry in the 200 to 450 nm range. The molar specific extinction of MI-1544 is 11,000 at 280 nm.

EXAMPLE 7

Preparation of {D-Lys[n-poly(N-vinylpyrrolidone-co-maleic Acid)-Gly-Phe-Leu-Gly (SEQ ID NO:5)]}$^6$,-GnRH (Abbreviated: P-GFLG-609)

Example 5 was followed, except that D-Lys$^6$-GnRH was used as GnRH analogue. The purity of the product was controlled by HPLC and the active ingredient content was determined by UV 20 spectrophotometry in the 200 to 450 nm range.

EXAMPLE 8

Preparation of D-Phe$^2$,D-Trp$^3$ {D-Lys[n-poly(N-vinylpyrrolidone-co-maleic Acid)-Gly-Phe-Leu-Gly-(SEQ ID NO:5)]}$^6$-GnRH (Abb.: P-GFLG-1004)

Example 5 was followed, except that SJ-1004 was used as GnRH analogue. The purity of the product was controlled by HPLC (Rt: 20.7 min, that of SJ-1004 is 17.3 min) and the active ingredient content was determined by UV spectrophotometry in the 200 to 450 nm range. The molar specific extinction of SJ-1004 is 6500 at 280 nm.

EXAMPLE 9

Preparation of {Lys[n-poly(N-vinylpyrrolidone-co-maleic Acid)-Gly-Phe-Leu-Gly-(SEQ ID NO:5)]}$^5$, cyclo(Asp$^6$-Lys$^8$)-GnRH-III (Abbr.: P-GFLG-614)

Example 5 was followed, except that TH-614 was used as GnRH analogue. The purity of the product was controlled by HPLC (Rt: of TH-614 is 16.4 min) and the active ingredient content was determined by UV spectrophotometry in the 200 to 450 nm range. The molar specific extinction of TH-614 is 8800 at 280 nm.

EXAMPLE 10

Preparation of {Lys[n-poly(N-vinylpyrrolidone-co-maleic Acid)-Gly-Phe-Leu-Gly-(SEQ ID NO:5)]}$^4$,-GnRH-III (Abbreviated: P-GFLG-685)

To the polymer solution prepared according to Example 1, 0.5 equivalent (calculated for the nitrophenyl ester groups) of HB-694 hormone analogue containing a free amino group was added. The pH value of the reaction mixture was adjusted to 10 by using (diisopropyl)-ethylamine. After a few hours piperidine was portionwise added to remove the protective group from the [Lys(n-Fmoc)]$^8$ derivative. After stirring for a few additional hours, the reaction mixture diluted with water was ultrafiltered and the ultrafiltration was repeated after dilution of the supernatant with sodium hydrogen carbonate solution. The thus-purified product was lyophilized, its purity was controlled by HPLC, and the active ingredient content was determined by UV spectrophotometry in the 200 to 450 nm 5 range. The molar specific extinction of HB-685 is 9800 at 280 nm.

EXAMPLE 11

Preparation of {Lys[n-poly(N-vinylpyrrolidone-co-maleic Acid)-Gly-Phe-Leu-Gly-(SEQ ID NO:5)]}$^8$,-GnRH-III (Abbr.: P-GFLG-602)

Example 5 was followed, except that TH-602 was used as GnRH analogue. The purity of the product was controlled by HPLC (Rt: 14.8 min, that of TH-602 is 13.4 min) and the active ingredient content was determined by UV spectrophotometry in the 200 to 450 nm range. The molar specific extinction of TH-602 is 9800 at 280 nm.

EXAMPLE 12

Preparation of Ac-D-Trp$^{1,3}$,D-Cpa$^2$,{Lys[n-poly(N-vinylpyrrolidone-co-maleic Acid)-Phe-Leu-Gly-])}$^5$, a-Asp (DEA)]$^6$, D-Ala$^{10}$-GnRH (Abbreviated: P-FLG-1892)

Example 5 was followed, except that the product prepared according to Example 2 was used as carrier and MI-1892 was employed as GnRH analogue. The purity of the product was controlled by HPLC (Rt: 30.77 min) and the active agent content was determined by spectrophotometry in the 200 to 450 nm range.

EXAMPLE 13

Preparation of Ac-D-Trp$^{1,3}$,D-Cpa$^2$,{Lys[n-poly(N-vinylpyrrolidone-co-maleic Acid)-Gly-Leu-Gly-]}$^5$, [a-Asp(DEA)]$^6$ D-Ala$^{10}$-GnRH (Abbreviated: P-GLG-1892)

Example 12 was followed, except that the product prepared in Example 3 was used as carrier and MI-1892 was employed as GnRH analogue. The purity of the product was controlled by HPLC (Rt: 25.39 min) and the active ingredient content was determined by UV spectrophotometry in the 200 to 450 nm range.

EXAMPLE 14

Preparation of Ac-D-Trp$^{1,3}$,D-Cpa$^2$,{Lys[n-poly(N-vinylpyrrolidone-co-maleic Acid)-Ahx]$^5$, [a-Asp(DEA)]}$^6$,D-Ala$^{10}$-GnRH (Abbreviated: P-Ahx-1892)

Example 12 was followed, except that the product prepared in Example 4 was used as carrier and MI-1892 was employed as GnRH analogue. The purity of the product was controlled by HPLC (Rt: 19.98 min) and the active ingredient content was determined by UV spectrophotometry in the 200 to 450 nm range.

EXAMPLE 15

Preparation of Ac-D-Trp$^{1,3}$,D-Cpa$^2${Lys[n-poly(N-vinylpyrrolidone-co-maleic Acid)-]}, [a-Asp(DEA)]$^6$,D-Ala$^{10}$-GnRH (Abbreviated: P-1892)

After dissolving poly(N-vinylpyrrolidone-co-maleic anhydride) in DMF, calculated amounts of MI-1892 and triethylamine were added. After standing for 12 hours the product was precipitated by diethyl ether, filtered, then dissolved in sodium hydrogen carbonate solution of 5% and purified as well as analyzed as described in the preceding Examples (Rt: 19.59 min).

EXAMPLE 16

Preparation of {Lys[n-poly(N-vinylpyrrolidone-co-maleic Acid)-Gly-Phe-Leu-Gly-(SEQ ID NO:5)]}$^5$, D-Trp$^6$-GnRH (Abbreviated: A-GFLG-615)

Example 5 was followed, except that TH-615 was used as GnRH analogue (see Example 9). d: 10300.

EXAMPLE 17

Preparation of Gly-Phe-Leu-Gly-(SEQ ID NO:5)-GnRH analogues coupled to the Poly(N-vinyl-pyrrolidone-co-maleic Acid)-hexylamide Derivative A calculated amount of hexylamine was added to the solution of poly(N-vinylpyrrolidone-co-maleic anhydride) in dimethyl formamide under stirring. After 2 hours the product was precipitated by adding diethyl ether, then filtered and washed with ether until it became amine-free (negative ninhydrin test, IR: 293 cm$^{-1}$ CH$_2$). The solid was again dissolved in DMF and H-Gly-Phe-Leu-Gly (SEQ ID NO:5) nitrophenyl ester hydrochloride was added. The pH value of the reaction mixture 20 was set to 7–8 with triethylamine and the precipitation was repeated after 3 hours. The coupling of the GnRH analogue and purification of the products were carried out as described in Example 5. The purity of the product was controlled by HPLC and the active agent content was determined by UV 25 spectrophotometry in the 200 to 450 nm range.

EXAMPLE 18

Investigation on the Dose-survival Relation

The investigation gives a precise information about the cell-damaging effect of the tested substance. In the case of cytostatics the cell-damaging effect is not cell-specific. GnRH analogues possess a phase-specific action, they block but do not kill the cells in the G0/G1 phase. One part of the arrested cells again go into the cycle, the other part may perish (apoptosis). The colonies formed from the arrested cells do not reach the countable colony size at the time of evaluation (the count of colonies may be identical but the sizes of colonies are different). In the case of hormone analogues, a specific inhibition of 10 to 30% can be achieved on the cells possessing a receptor for the hormone in question. The investigations were carried out on MCF-7 and MDA-MB-231 human mammary carcinoma cell lines, PC3 human prostate 15 carcinoma cell line and Ishikawa human endometrium carcinoma cell line. Three hundred cells were set into Petri dishes of 3.5 cm in diameter each. The treatment was carried out once, 24 hours following the explantation, then the colonies formed were counted after 9 to 12 days.

After dissolving the substances in the nutrient medium, the cultures were treated with 1 to 50 μM of MI-1544 human GnRH antagonist; MI-1892 chicken GnRH antagonist; SJ-1004 human GnRH antagonist analogues and synthetic lamprey GnRH-III substance as well as with Lys$^4$-GnRH-III and Lys$^5$-cyclo(Asp$^6$,Lys$^8$)-GnRH-III lamprey GnRH-III analogues; furthermore P-GFLG-1544, P-GFLG-1892, P-GFLG-GnRH-III, P-GFLG-Lys$^4$-GnRH-III, P-GFLG-Lys$^5$-cyclo(Asp$^6$,Lys$^8$)-GnRH-III conjugates or P-FLG-1892 and P-GLG-1892 conjugates, respectively, corresponding to the same amounts of the active substances.

MI-1892 chicken GnRH antagonist substance (administered in a concentration of 50 μm) inhibited the colony formation of both mammary carcinoma cell cultures (MCF-7, MDA-MB-231) to a nearly identical degree, namely by 15 to 20% and 35 to 38%, respectively. When administering in a concentration of 50 μM, the MI-1544 hGnRH antagonist showed an inhibition of 45% of the colony formation on the MCF-7 cell line and 20% on the MDA-MB-231 cell line.

Both conjugates P-GFLG-1544 and P-GFLG-1892 exerted an inhibition of 80 to 85% on the colony formation in a concentration of 10 μM and 100% inhibition in a concentration of 50 μM of the active substance, respectively, (Table 1).

TABLE I

Inhibition of colony formation by GnRH analogue/macromolecule conjugates (P-GFLG-GnRH analogues) on human tumour cell lines

| Exam. No. (comp.) | Cell line | Dose (μM) | % Inhibition |
|---|---|---|---|
| 6. P-GFLG-1544 | MCF-7 | 10 | 85 |
|  |  | 50 | 100 |
|  | MDA-MB-231 | 10 | 80 |
|  |  | 50 | 100 |
|  | Ishikawa | 50 | 100 |
|  | PC3 | 10 | 100 |
|  |  | 50 | 100 |
| 5. P-GFLG-1892 | MCF-7 | 10 | 60 |
|  |  | 50 | 93 |
|  | MDA-MB-231 | 10 | 92 |
|  |  | 30 | 100 |
|  | Ishikawa | 10 | 72 |
|  |  | 30 | 100 |
|  | PC3 | 10 | 86 |
| 8. P-GFLG-1004 | MCF-7 | 10 | 75 |
|  |  | 50 | 95 |
|  | MDA-MB-231 | 10 | 62 |
|  |  | 50 | 92 |

TABLE I-continued

Inhibition of colony formation by GnRH analogue/macromolecule conjugates (P-GFLG-GnRH analogues) on human tumour cell lines

| Exam. No. (comp.) | Cell line | Dose ($\mu$M) | % Inhibition |
|---|---|---|---|
| | Ishikawa | 10 | 3 |
| | | 50 | 46 |
| | PC3 | 30 | 100 |
| | | 50 | 100 |
| 11. P-GFLG-GnRH-III | MCF-7 | 50 | 9 |
| | Ishikawa | 50 | 15 |
| | PC3 | 50 | 16 |
| 10. P-GFLG-Lys$^4$-GnRH-III | MCF-7 | 50 | 68 |
| | MDA-MB-231 | 50 | 75 |
| | Ishikawa | 50 | 25 |
| | PC3 | 30 | 94 |
| 9. P-GFLG-Lys$^5$-cyclo(Asp$^6$,Lys$^8$)-GnRH-III | MCF-7 | 50 | 78 |
| | MDA-MB-23 1 | 50 | 82 |
| | Ishikawa | 50 | 19 |
| | PC3 | 50 | 100 |

The tripeptide spacer-containing conjugates P-FLG-1892 and P-GLG-1892 exerted a somewhat weaker, namely 70 to 80%, inhibition on the survival of the cells in an active substance concentration of 50 $\mu$M. P-GFLG-1544 and P-GFLG-1892 were the most strong 20 inhibitors of colony formation on PC3 prostate and Ishikawa endometrium carcinoma cell lines, too: by using a concentration of 30 to 50 $\mu$M, an inhibition of 100% was observed both in the PC3 and the Ishikawa cell cultures (Table 1). Both conjugates highly surpassed the inhibition of 25 colony formation of MI-1544 GnRH antagonist and MI-1892 chicken GnRH antagonist analogue active substances, which has been found to be 5% and 10%, respectively, on Ishikawa cell line and 20% or 5%, respectively, on the PC3 cell line by 37 using a concentration of 50 $\mu$M.

When administered in a concentration of 50 $\mu$M, SJ-1004 as a weak GnRH antagonist analogue substance inhibited the degree of colony formation by 31% on the MCF-7 cell line and 5 by 26% on the MDA-MB-231 cell line whereas it did not show any inhibition on the PC3 cell line (0%) or on Ishikawa cell line (5%), respectively. In contrast to this, when given in an active substance concentration of 50 $\mu$M, the P-GFLG-1004 conjugate resulted in 10 an inhibition of 92 to 95% on mammary carcinoma cell lines; 100% on PC3 prostate carcinoma cell culture; and 46% on Ishikawa cell line (Table 1). In opposition to the own or human and chicken GnRH analogues, the synthetic lamprey GnRH-III resulted in the most significant inhibition of colony formation as the active substance in itself but not as a conjugate on the MCF-7, MDA-MB-231 and PC3 cell lines. At a concentration of 50 $\mu$m, GnRH-III inhibited the colony formation by 65% (on MCF-7), 69% (on MDA-MB-231) and 21% (on PC3), respectively, whereas 20 the P-GFLG-GnRH-III conjugate did not result in an inhibition of higher than 16% on any cell line (Table 1).

In the cases of Lys$^4$-GnRH-III and Lys$^5$-cyclo(Asp$^6$,Lys$^8$)-GnRH-III lamprey GnRH-III analogues, the inhibiting effects of the conjugates, namely, P-GFLG-Lys$^4$-GnRH-III and P-GFLG-25 Lys$^5$-cyclo(Asp$^6$,Lys$^8$)-GnRH-III proved again to be more significant (Table 1). In the form of active substance, Lys$^4$-GnRH-III exerted on the colony formation an inhibition of 40% on the MCF-7 cell line, 35% in the MDA-MB-231 cell culture 38 and 21% respectively, on Ishikawa cells. It did not show any inhibition in the case of PC3 cells.

The P-GFLG-Lys$^4$-GnRH-III conjugate showed on the colony formation an inhibition of 68% on MCF-7 cell line, 75% on 5 MDA-M8-231 cell culture and 25% on Ishikawa cells; interestingly, it inhibited by 94% the colony formation on the PC3 cell line (Table 1).

The Lys$^5$-cyclo(Asp$^6$,Lys$^8$)-GnRH-III lamprey analogue exerted on the colony formation an inhibition of 44% on MCF-7 cell line and 13% on Ishikawa cell line. As a conjugate, P-GFLG-Lys$^5$-cyclo(Asp$^6$,Lys$^8$)-GnRH-III inhibited the colony formation in mammary carcinoma cell cultures much more strongly (78 to 82%) than the active substance. On Ishikawa cell line, the inhibiting effect of the conjugate (19%) was newly the same an that of the active substance (13%). The conjugate blocked the colony formation by 100% on the PC3 cell line.

EXAMPLE 19

In vitro Inhibition of Proliferation of the Human Mammary Carcinoma Cell Line

The procedure of treatment was as follows. After trypsinization the cells, 400,000 cells of MCF-7, MDA-MB-231 human mammary carcinoma, PC3 human prostate carcinoma or Ishikawa human endometrium tumour each were passed into Petri dishes of 10 cm in diameter. Starting from the day following transfer, the cells were treated with the substances to be tested in solution prepared with the nutrient medium during the exponential growth phase. The cultures were treated with 1 to 50 $\mu$M (calculated for the total volume of the culture) of MI-1544 GnRH antagonist, MI-1892 chicken GnRH antagonist or SJ-1004 GnRH antagonist analogues as well as synthetic lamprey GnRH-III hormone in every two days and the cell count was determined on the 7th day. Simultaneously with the above examinations, the cells were once treated with the conjugates P-GFLG-1544, P-GFLG-1892, P-GFLG-1004 as well as P-GFLG-GnRH-III in amounts corresponding to 1 to 50 $\mu$M of active substance on the day following transfer, then the cell count was determined on the 7th day after explantation. The GnRH peptide hormone substances used in a concentration of 30 $\mu$M resulted in the most significant inhibition of cell proliferation. The inhibitory effect was not enhanced by increasing the concentration.

In the case of the MCF-7 estradiol receptor (ER)-positive human cell line (10% FCS), a significant difference was observed between the direct antitumour effect of the weak GnRH antagonist SJ-1004 and the GnRH antagonist MI-1544 or chicken GnRH antagonist MI-1892, respectively. SJ-1004 elicited only a decrease of 17% in the cell count whereas both antagonists (30 $\mu$M) resulted in a 34 to 36% inhibition in the case of a treatment carried out every other day for five days.

When used in the same dose of the active substance, P-GFLG-1544 conjugate induced an inhibition of 58%. It may be supposed that the antitumour effect of MI-1544 antagonist is additively strengthened by the copolymer covalently bound thereto (Table II).

When administered in a concentration of 30 $\mu$M of the active substance, the P-GFLG-1892 conjugate containing MI-1892 showed 45% inhibition on the cell proliferation. Considering that one single treatment was performed with the conjugate, the polymer improved the inhibitory effect of the antagonist in this case, too (Table II).

TABLE II

Inhibition of cell division by GnRH analogue/macromolecule conjugates on various human tumour cell lines

| Exam. No. | (compd.) | Cell line | Dose (μM) | % Inhibition |
|---|---|---|---|---|
| 6. | P-GFLG-1544 | MCF-7 | 30 | 58 |
|  |  | MDA-MB-231 | 30 | 45 |
|  |  | Ishikawa | 30 | 95 |
|  |  | PC3 | 30 | 68.5 |
| 5. | P-GFLG-1892 | MCF-7 | 30 | 45 |
|  |  | MDA-MB-231 | 30 | 42 |
|  |  | Ishikawa | 30 | 91 |
|  |  | PC3 | 30 | 51 |
| 8. | P-GFLG-1004 | MCF-7 | 30 | 63 |
|  |  | MDA-MB-231 | 30 | 68 |
|  |  | Ishikawa | 30 | 20 |
|  |  | PC3 | 30 | 35 |
| 11. | P-GFLG-GnRH-III | MCF-7 | 30 | 10 |
|  |  | MDA-MB-231 | 30 | 11 |
| 13. | P-6LG-MI-1892 | MCF-7 | 30 | 33 |
|  |  | MDA-MB-231 | 30 | 35 |
| 12. | P-FLG-MI-1892 | MCF-7 | 30 | 33 |
|  |  | MDA-MB-231 | 30 | 35 |

MCF-7: mammary tumour cell line of human origin; MDA-MB-231: mammary tumour cell line of human origin; PC3: prostate tumour cell line of human origin; Ishikawa: endometrium tumour cell line of human origin.

P-FLG-1892 and P-GLG-1892 conjugates containing a tripeptide spacer group and given in an active substance content of 30 μM resulted in a direct antitumour effect of only 30 to 35% (Table 2). In the case of MDA-MB-231 ER-negative cells (10% FCS), the treatment in every two days with SJ-1004 resulted in a decrease of 23% of the cell count, whereas the treatment with MI-1544 and MI-1892 (30 μM) decreased the cell count by 35% to 36%.

When administered in an active substance concentration of 30 μM, P-GFLG-1544 conjugate resulted in 45% and P-GFLG-1892 in 42% inhibition of the proliferation (Table II). By using P-FLG-1892 or P-GLG-1892 a lower, namely 33 to 35%, inhibition was seen (Table II).

On the PC3 prostate and Ishikawa endometrium carcinoma cell lines, the proliferation-inhibiting effect of the effective GnRH-analogue substances (MI-1544 and MI-1892) was significantly increased by the copolymer covalently coupled thereto. When used in a concentration of 30 μM, after two treatments on days 2 and 4, MI-1544 inhibited the proliferation of Ishikawa cell line by 8% and that of the PC3 cell line by 24%; whereas P-GFLG-1544 once administered resulted in a direct inhibition of 95% of the proliferation on Ishikawa cell line and 68.5% on the PC3 cell line.

After two treatments, the MI-1892 chicken GnRH antagonist active substance resulted in a 14% and 33% inhibition on Ishikawa or PC3 cell cultures, respectively. After a single administration the P-GFLG-1892 conjugate exerted a direct proliferation-inhibiting effect of 51% on the PC3 cell line and a more significant inhibition of 91%, respectively, on Ishikawa cell line (Table II).

SJ-1004 as a weak GnRH antagonist showed a weak antitumour effect. After two treatments (days 2 and 4), an inhibition of only 17% was observed on the MCF-7 cell line whereas this inhibition was found to be 23% on the MDA-MB-231 cell line, 20% on Ishikawa cell line and 10% on PC3 cell line, respectively. When administered once in the conjugate form, P-GFLG-1004 resulted in a nearly identical significant inhibition (63 to 68%) on both mammary carcinoma cell lines (Table II).

The P-GFLG-1004 conjugate exerted a weaker direct proliferation-inhibiting effect than P-GFLG-1554 or P-GFLG-1892; this was found to be 35% on PC3 and 20% on Ishikawa cell line, respectively. In the conjugates of the GnRH-III synthetic lamprey GnRH or P-GFLG-GnRH-III, the investigation on the proliferation-inhibiting effect was carried out only on the MCF-7 and MDA-MB-231 cell lines. In agreement with investigations on the inhibition of colony formation, this was the single GnRH hormone out of the agonistic and antagonistic derivatives tested, which showed as the active substance alone a more significant inhibition of colony formation or proliferation, respectively, in comparison to the results achieved with the P-GFLG-GnRH-III conjugate. By using the active substance, two treatments (days 2 and 4) resulted in a direct inhibition of 40 to 39% whereas an inhibition of 10 to 11% was only observed after one treatment (on day 2) with P-GFLG-GnRH-III (Table II).

As shown in Table II, the proliferation-inhibiting effect is in agreement with the results of inhibition of the colony formation within a certain error. Based on our observations, a strict correlation exists also between the inhibition of colony formation and the in vivo effect of the substances, too.

EXAMPLE 20

The in vivo Toxicological Study of the P-GFLG-1892 and P-GFLG-1544 Conjugates

These experiments were carried out on 21 control and 20 treated female CBA/Ca mice each. The treatments were as follows: 7 animals as controls without treatment; 7 animals once administered subcutaneously (s.c.) with the 10-fold of the effective dose (active substance concentration: 400 μg/animal); 7 animals once administered intraperitoneally (i.p.) with the 10-fold of the effective dose (active substance concentration: 400 μg/animal). None of the substances proved to be toxic. On the 5th day following the i.p. treatment and on the 7th day following the s.c. treatment, the body weights of the animals were increased by 10% whereas the weights of the control animals did not change.

EXAMPLE 21

Investigation on the in vivo Antitumour Effect of P-GFLG-1892 and P-GFLG-1544 Conjugates on Immunosuppressed Mice Bearing Human MCF-7 or MDA-MB-231 Xenograft When inoculated to immunosuppressed CBA/Ca mice, the MCF-7 and MDA-MB-231 cells had formed a tumour which could successfully be transplanted. The immunosuppression of mice was carried out by using the method of Steel et al. [Br. J. Cancer, 37, 224–230 (1978)].

Immunosuppression and Xeno-transplantation.

CBA/Ca female mice of about 6 weeks old were thymectomized and then, after one week, they were irradiated with 60Co (whole body irradiation; the lethal dose is 9.5 Gray). Whin 24 hours 3 to $5 \times 10^5$ myelocytes were injected to the animals. Beneath the skin of the immunosuppressed mice $2 \times 10^7$ tumour cells or, in the case of later passages, about 2 $mm^3$ of tumour cells or in the case of later, additional passages about 2 $mm^3$ of tumour pieces were implanted. After xeno-transplantation the mice bearing MCF-7 xenograft were treated weakly once with the mixture of 50 µg of estradiol valerate and 30 µg of Norgestomet (Intervet International B.V.). The treatment with steroid hormone was stopped by at least one week before beginning the investigation. (The take usually occurred during 24 days.)

In the case of MCF-7 tumours (xenografts) the examinations were carried out with passages being in the phase of the 37th and 38th, respectively, transplantations. Based on the observations, the growth of tumours was accelerated after transplantation of several years and showed a two-fold growth rate in comparison to the state after the 4th or 5th passage. (In the case of control animals the tumour after 4–5 passages grew from 0.3 g to 3–4 g whereas the weights of tumours after the 37th or 38th transplantation increased from 0.3 g to 8 g during 6 weeks). It should be noted that likely, a clonal selection occurred during the passages; namely, clones growing more rapidly prevailed the slower-growing populations (clonal selection).

In the case of mice bearing MCF-7 xenograft, the treatment was begun in the 4th week following xeno-transplantation. This examination was carried out on 50 animals (with a tumour volume of 255 to 319 mm³; (d12× d2×3.14):6]. The treatments were carried out as follows. Daily twice MI-1892 (2×25 µg in every 12th hour) s.c. given to 8 animals each; daily 50 µg or in every 3rd day 150 µg of P-GFLG-1892 or P-GFLG-1544 conjugate (calculated for the active substance) to 8 animals or 6 animals each, respectively; P-GFLG-OH given daily in an s.c. dose corresponding to 50 µg of active substance to 6 animals each; and 150 µl of physiological saline daily administered s.c. to 8 control animals each. At the end of the 4th week of treatment the daily two treatments with the MI-1892 antagonist substrate and the daily single treatment with P-GFLG-1892 and P-GFLG-1544 conjugates resulted in a decrease of 20 to 30% in the tumour volume in comparison to the tumour volume of controls of the same age. Thus, the treatments diminished the rate of tumour growth in such a manner that the substance administered daily twice and the conjugate administered daily once led to about the same result. (The former treatment caused a decrease of 20%, the latter one a decrease of 30%, respectively, in the tumour growth.) The rate of tumour growth was not influenced by P-GFLG-1892 or P-GFLG-1544 given in every 3rd day or by daily given P-GFLG-OH.

Recent investigations have begun on 28 animals bearing MCF-7 xenograft and on 28 animals bearing MDA-MB-231 xenograft. On animals bearing MCF-7 tumour the treatment was commenced in the 5th week following xeno-transplantation; the tumour volume was 205 to 225 mm³. On animals bearing MDA-MB-231 tumour, the treatment was started in the 4th week after xeno-transplantation with a turnour volume of 140 to 150 mm3. The treatments were carried out in such a manner that daily 75 µg of P-GFLG-1892 conjugate s.c. (calculated for the active substance) or daily 50 pg, respectively, of P-GFLG-1544 conjugate s.c. (calculated for the active substance) or daily 50 µg, respectively, of P-GFLG-OH carrier s.c. (calculated for the active substance) were used. The control groups were daily treated with physiological saline s.c. (Each treated group consisted of 7 animals).

It should be emphasized at repeated investigations carried out on mice bearing MCF-7 xenograft that both conjugates P-GFLG-1892 and P-GFLG-1544 resulted in a 30 to 35% inhibition of tumour growth even in the 2nd week of treatment (Table 3). By exceeding the results of former investigations in the 4th week, the decrease caused by P-GFLG-1892 was 37% (the tumour volume was 2.428 cm³), the decrease caused by P-GFLG-1544 was 49% (the tumour volume was 1.806 cm³) in the tumour volumes in comparison to controls to of the same age. In the 6th week, the inhibitory effects of both conjugates were found to be essentially equal; even a tumour-free animal was found in the case of P-GFLG-1544. A 43 to 49% inhibition of tumour growth was achieved (Table III).

TABLE III

Effect of the tumour growth on MCF-7 xenograft

| Example No. 5 (compound) | Treatment weeks | Tumour volume as control % | Inhibition % |
|---|---|---|---|
| MI-1892 | 4 | 78.5 | 22.5 |
| 2 × 25 µg | 6 | 79 | 21 |
| 5. P-GFLG-1892 | 2 | 70 | 30 |
| 1 × 50 µg | 6 | 57 | 43 |
| 6. P-GFLG-1544 | 2 | 70 | 30 |
| 1 × 50 µg | 6 | 51 | 49 |

Xenograft: transplantation of human tumour into immunosuppressed mice.

TABLE IV

Effect on the tumour growth on MDA-MB-231 xenograft

| | Tumour volume (cm³) as control (%) weeks | | | | | | | |
|---|---|---|---|---|---|---|---|---|
| Example No. (compd) | 0 | 1 | 2 | 3 | 4 | 5 | 6 | 7 |
| 6. P-GFLG-1544 | 0.15 | 0.21 | 0.21 | 0.24 | 0.28 | 0.33 | 0.36 | — |
| 1 × 50 µg (%) | 100 | 83 | 66 | 66 | 67 | 75 | 63 | — |
| 5. P-GFLG-1892 | 0.15 | 0.21 | 0.25 | 0.27 | 0.34 | 0.33 | 0.33 | — |
| 1 × 75 µg (%) | 100 | 84 | 79 | 74 | 81 | 75 | 58 | — |
| Control | 0.15 | 0.25 | 0.32 | 0.37 | 0.41 | 0.45 | 0.57 | — |
| 11. P-GFLG-GnRH-III | 0.17 | 0.25 | 0.33 | 0.40 | 0.41 | 0.49 | 0.40 | 0.31 |
| 1 × 100 µg (%) | 104 | 107 | 80 | 72 | 64 | 53 | 32 | 24 |
| GnRH-III | 0.19 | 0.26 | 0.36 | 0.47 | 0.55 | 0.81 | 1.04 | 1.28 |
| (%) | 115 | 113 | 86 | 85 | 85 | 87 | 85 | 101 |
| 6. P-GFLG-1544 | 0.17 | 0.24 | 0.3 | 0.36 | 0.35 | 0.46 | 0.58 | 0.75 |
| 1 × 100 µg (%) | 101 | 105 | 72 | 65 | 53 | 49 | 47 | 59 |
| Control | 0.17 | 0.23 | 0.42 | 0.56 | 0.65 | 0.93 | 1.23 | 1.27 |

Xenograft: transplantation of human tumour into immunosuppressed mice. The animals were daily treated in s.c. route.

TABLE V

Effect on the tumor growth on MDA-MB-231 xenograft

| Example No. 5 (compound) | Treatment weeks | Tumour volume as control % | Inhibition % |
|---|---|---|---|
| MI-1892 | 4 | 75.5 | 24.5 |
| 2 × 25 µg | 6 | 78 | 22 |
| 5. P-GFLG-1892 | 2 | 73.5 | 26.5 |
| 1 × 50 µg | 6 | 56 | 44 |
| 6. P-GFLG-1544 | 2 | 76.5 | 23.5 |
| 1 × 50 µg | 6 | 60 | 40 |
| 6. P-GFLG-1544 | 2 | 71 | 29 |
| 1 × 100 µg | 6 | 47 | 53 |
| 11. P-GFLG-GnRH-III | 2 | 80 | 20 |
| 1 × 100 µg | 4 | 64 | 36 |
|  | 6 | 33 | 67 |
| GnRH-III | 2 | 86 | 14 |
|  | 4 | 85 | 15 |
|  | 6 | 85 | 15 |

Xenograft: transplantation of human tumour into immunosuppressed mice. The animals were daily treated in s.c. route.

Volumes and weights of tumours after 6-week treatment

|  | Volume (cm$^3$) | Weight (g) |
|---|---|---|
| Treated with P-GFLG-1892 | 4.327 + 0.379 | 4.0 + 0.9 |
| Treated with P-GFLG-1544 | 3.502 + 0.321 | 4.8 + 0.8 |
| Control | 6.868 + 0.573 | 7.9 + 0.8 |

In the case of mice bearing MDA-MB-231 tumour, a 21 to 34% decrease in the tumour volume was observed even from the 2nd week in comparison to the control group of the same 20 age (Table IV). The growth of the tumours (estradiol receptor-negative, estradiol-independent tumours) was not inhibited by chemical castration; therefore, the effect observed was unequivocally the result of a direct antitumour action. The treatment was terminated in the 6th week; nearly the same inhibition of 37 to 42% was observed after the treatment with two conjugates (P-GFLG-1892 and P-GFLG-1544, respectively) (Table 111). A tumour-free animal was found at the end of the 6th week in the groups treated with the conjugates.

A more recent study was started on 28 animals bearing MDA-MB-231 xenograft. The treatment was begun in the 4th or 5th week following xenotransplantation. The tumour volume was 0.165 to 0.194 cm$^3$. The treatments were carried out daily with 100 jg of active substances (calculated to GnRH-III, P-GFLG-GnRH-III or P-GFLG-1544, respectively) administered in s.c. route. (For treatment of the control group, see the preceding Examples). Each group consisted of 7 animals. During the treatments the 10 tumour volumes were weakly measured for 9 weeks. The results are summarized in Table III.

The GnRH-III active substances in themselves did not inhibit the rate of tumour growth. The increase in the dose of P-GFLG-1544 GnRH antagonist conjugate (50 µg in the preceding series, 100 µg in this series of experiments) did not raise the inhibitory effect of the conjugate on tumour growth. It is considered to be a very important result that 2 animals from 7 ones treated with P-GFLG-GnRH-III and 1 animal from 7 ones treated with P-GFLG-1544 became tumour-free in 20 the 6th week of treatment. Volumes and weights of tumours after 9-week treatment Volumes and weights of tumours after 9-week treatment

|  | Volume (cm$^3$) | Weight (g) |
|---|---|---|
| P-GFLG-GnRH-IIII | 0.613 + 0.307 | 0.45 + 0.4 |
| GnRH-III | 2.017 + 0.585 | 1.84 + 0.52 |
| P-GFLG-1544 | 1.618 + 0.518 | 0.94 + 0.52 |
| Control | 2.249 + 0.787 | 1.505 + 0.29 |

An excellent 73 to 78% inhibition, not observed until now, was obtained with the P-GFLG-GnRH-III conjugate at the end of the 9th week. No significant difference was found between the body weights of treated and control animals, respectively, either during the treatment or at the termination of treatment.

EXAMPLE 25

Investigation on the in vivo Antitumour Effect of P-GFLG-1892 and P-GFLG-1544 on Mice Bearing MXT Mouse Mammary Tumour When inoculated to CBA/Ca mice, the MXT mouse mammary 10 tumour cells developed a tumour. The take of tumour occurred in 100%; thus, the treatments could be started before the development of tumours, on the day following xenotransplantation. A further importance of the model lies therein that, in opposition to the immune system of mice bearing human xenograft, the immune system of mice bearing MXT mouse mammary tumor was not artificially suppressed; therefore, this model was equally useful to investigate the antitumour effect as well as the action exerted on the immune system. The MXT mouse mammary carcinoma contains ER and PgR proteins; furthermore, it contains also GnRH receptors; therefore, this in vivo tumor model is suitable for studying both the direct and indirect effects. The treatment of mice bearing MXT mammary tumour was commenced on the day following transplantation. The investigation was accomplished on 35 animals in such a way that 75 µg of MI-1892, MI-1544, P-GFLG-1892 and P-GFLG-1544, respectively (calculated for the active substances), were s.c. injected daily once to each mouse while the tumour volume was systematically measured from the 9th day of treatment. The results are shown in Table VI.

TABLE VI

Effect on the tumour growth on MDA-MB-231 xenograft

| Example No. (compound) | Tumour volume (cm$^3$) as control (%) days | | | | | | | |
|---|---|---|---|---|---|---|---|---|
|  | 9 | 11 | 13 | 17 | 18 | 20 | 24 | 26 |
| P-GFLG-1544 | 0.38 | 0.74 | 1.26 | 2.43 | 3.91 | 4.74 | 7.34 | 9.03 |
| (%) | 55 | 41 | 39 | 46 | 52 | 51 | 58 | 65 |
| P-GFLG-1892 | 0.29 | 0.66 | 0.91 | 1.86 | 3.1 | 3.61 | 6.07 | 8.91 |
| (%) | 40 | 36 | 28 | 36 | 42 | 38 | 48 | 64 |
| Control | 0.7 | 1.8 | 3.22 | 5.11 | 7.42 | 9.26 | 12.66 | 13.82 |
| MI-1544 | 0.44 | 1.03 | 1.74 | 2.63 | 3.94 | 5.02 | 6.08 | 8.42 |
| (%) | 63 | 57 | 54 | 51 | 53 | 54 | 48 | 60 |
| MI-1892 | 0.61 | 1.05 | 1.59 | 3.17 | 4.8 | 5.73 | 6.32 | 11.30 |
| (%) | 86 | 58 | 49 | 62 | 64 | 61 | 50 | 82 |

The animals were daily treated in s.c. route starting from the day following transplantation of MXT mouse mammary tumour. The treatment was performed as follows: P-GFLG-1544: 75 µg/day/animal related to MI-1544 active substance; P-GFLG-1892: 75 µg/day/animal related to MI-1892 active substance; MI-1544: 75 µg/day/animal; MI-1892: 75 µg/day/animal.

The percentages of inhibition are summarized in Table VII. The strongest inhibition of tumour growth was observed at the end of the 2nd week of treatment. The percentages of inhibition measured at the end of 2nd and 3rd weeks are shown in Table VII. The results show that, in this model, the P-GFLG-1892 conjugate is much more effective than MI-1892 active substance in itself. No difference exists between the inhibitory effect of MI-1544 and that of P-GFLG-1544.

TABLE VII

Effect on the tumour growth on MXT mouse mammary tumour

| Example No. 5 (compound) | Treatment weeks | Tumour volume as control % | Inhibition % |
|---|---|---|---|
| MI-1892 | 13 | 49 | 51 |
| 1 × 75 µg | 20 | 61 | 39 |
| MI-1544 | 13 | 54 | 46 |
| 1 × 75 µg | 20 | 54 | 46 |
| 5. P-GFLG-1892 | 13 | 28 | 72 |
| 1 × 75 µg | 20 | 38 | 62 |
| 6. P-GFLG-1544 | 13 | 39 | 61 |
| 1 × 75 µg | 20 | 51 | 49 |

The animals were daily treated in s.c. route starting from the day following transplantation of the MXT mouse tumour.

EXAMPLE 26

Preparation of [Lys(ε-Fmoc)]$^5$-GnRH-III

The peptide is prepared on a benzhydrylamine resin (of 0.65 milliequivalent/g capacity) by using an automatic peptide synthetizer. The protected amino acid Boc-glycine is used in an excess of three equivalents calculated for the capacity of the resin; DIC as condensing agent and HOBt as catalyst are employed in amounts equivalent to the protected amino acid. The coupling of Boc-Gly-OH to the resin lasts for 12 hours. Thereafter, the completion of coupling to the resin is controlled by means of ninhydrin reaction of the resin/protected amino acid compound. The coupling to the resin of Boc-Gly-OH is usually complete in the first coupling; if in some cases the ninhydrin reaction gives a positive result (indicating that the amino groups of the benzhydrylamine resin are not fully substituted), the coupling to the resin can be made complete by using the symmetric anhydride method. (Based on the weight increase, the capacity of the resin amounts to 75–80% of the capacity value given by the manufacturing company.) After cleaving and neutralizing the Boc-Gly-BHA resin in the usual way, the peptide synthesis is carried out stepwise according to the following scheme:

| | Minutes |
|---|---|
| 1. washing 3 times with dichloromethane | 2 |
| 2. cleavage once with a mixture of 1:2 ratio by volume of TFA and dichloromethane | 2 |

-continued

| | Minutes |
|---|---|
| 3. cleavage once with a mixture of 1:2 ratio by volume of TFA and dichloromethane | |
| 4. washing 3 times with dichloromethane | 2 |
| 5. washing 3 times with ethanol | 2 |
| 6. washing 3 times with chloroform | 2 |
| 7. neutralization twice with a mixture of 1:9 ratio by volume of triethylamine and chloroform | 3 |
| 8. washing twice with chloroform | 2 |
| 9. washing 3 times with dichloromethane | 2 |
| 10. addition of Boc-amino acid | |
| 11. coupling once with diisopropylcarbodiimide | 120–300 |
| 13. washing with ethanol | |

On cleaving the Boc protective group, a mixture of 0.5 10% by weight of indole with 0.2% by volume of thioanisole or a mixture of 2% by volume of anisole with 0.2% by weight of L-methionine is employed for preventing side reactions. Protected amino acids are usually coupled by employing the carbodiimide method, but BOP reagent is used for bulky amino acids (with high steric demand) (e.g. Leu, Trp, Cpa).

In the case of a positive ninhydrin reaction, the coupling is carried out with symmetric anhydride after carbodiimide coupling; or with BOP reagent after BOP-reagent coupling. In the course of the synthesis, a dimethylformamide (DMF) solution containing a three-fold excess of Boc-amino acid, molar ratio of DIC coupling agent and HOBt catalyst calculated for 0.5 mmol of BHA resin are used in an order according to the sequence. In the present Example, Boc-L-Lys(ε-Fmoc)-OH protected amino acid is used as amino acid in position 5.

The protective groups of the side chains and the peptide are removed from the resin by liquid HF in such a way that 0.25 mmole of peptide-BHA resin is maintained in 20–25 ml of HF in the presence of 2.5 ml of 10% by weight of p-cresol containing anisole and 100 mg of dithiothreitol at 0C for 1 hour. After removing HF under reduced pressure and treating the residue with absolute diethyl ether, the peptide is dissolved from the solid residue in a 15–33% by volume acetic acid solution. In the present case, the hydrofluoride salt of the peptide is purified by gel filtration on Sephadex G-25 column in 33% by weight acetic acid to obtain 360 mg of crude product with a chemical purity of 85%; Rf=0.5. Subsequently, the peptide is purified by using medium-pressure liquid chromatography (MPLC) on C 18 reverse-phase silica gel column with gradient solutions.

EXAMPLE 27

Preparation of Lys$^5$-GnRH-III

After dissolving 240 mg of crude intermediary peptide derivative in 10 ml of DMF-water mixture of 1:1 ratio, 2 ml of piperidine are added while stirring and cooling with ice-water. After 2.5 hours the mixture is evaporated and the residue dissolved in 33% acetic acid and purified on a Sephadex G-25 column. The fractions are investigated by means of TLC and the main product is collected. The crude product is purified by using MPLC procedure.

The conditions of the column included: Prepex C-18 (25–40µ, Phenomenex, USA) Column: 400 mm (in length)× 25 mm (in diameter) Eluent A: 70% by vol. of 0.05 M ammonium acetate solution (pH 4.00) and 30% by vol. of methanol B: 50% by vol. of 0.05 M ammonium acetate solution (pH 4.00) and 50% by vol. of methanol.

The elution is carried out by gradient elution with an eluent composed of solutions A and B. The pure main fraction is collected, then made free from salts and purified by carrying out gradient elution on the above column. Eluent: A: 10% acetic acid 400 ml B: a 80:20 mixture of A and isopropanol 400 ml. The pure fractions are collected and the residue is lyophilized to give 77 mg of the aimed product; $R_{f1}$=0.40, $R_{f2}$=0.15.

EXAMPLE 28

Preparation of Lys$^5$,cyclo[Asp$^6$-Lys$^8$]-GnRH-III a) The crude intermediary peptide derivative (120 mg) described in Example 26 is transformed to its hydrochloride salt by dissolving the peptide 1 in 6 ml of water and adding 2 ml of 0.1 N hydrochloric acid solution. After evaporation of the solution to dryness under reduced pressure, 102 mg of hydrochloride salt are obtained; $R_{f2}$=0.5.

b) Cyclization: A solution containing 29 mg of peptide hydrochloride of step 3/a) in 25 ml of DMF is cooled to 0° C. and 200 μl of 1% sodium hydrogen carbonate'solution are added. Simultaneously, 10 mg of BOP reagent and 10 mg of 1- hydroxybenzotriazole are dissolved in 5 ml of DMF and added slowly, portionwise to the above aqueous solution. Subsequently, from a stock solution containing 170 μl of diisopropyl ethylamine (DIEA) and 5 ml of DMF, 200 μl are added to the reaction mixture which is then stirred at room temperature overnight. The intermediary peptide formed ($R_{f2}$=0.6) is subjected to the next transformation without isolation.

c) Removal of the Fmoc group. After evaporating the reaction mixture 3/b) under reduced pressure, the residue is triturated with ethyl acetate and filtered. The solid is dissolved in 5 ml of DMF, then a mixture of 5 ml of DMF with 200 μl of piperidine is added and the reaction mixture is evaporated under reduced pressure. The residue is dissolved in 33% by volume acetic acid and purified on a Sephadex G-25 column. The fractions containing the main product are further purified by using MPLC method.

Eluent A: 70% by vol. of 0.05 M ammonium acetate solution and 30% by vol. of methanol B: 30% by vol. of 0.05 M ammonium acetate solution and 70% by vol. of methanol. The pure fractions are lyophilized twice to obtain 11 mg of the aimed product; $R_{f2}$=0.35, $R_{f7}$=0.187.

EXAMPLE 29

Preparation of Lys$^5$[Lys(ε-Fmoc)]$^8$-GnRH-III

The method described in Example 26 is followed with the difference that Boc-L-Lys(ε-Fmoc)-OH is used instead of Boc-L-Lys(ε-Z)-OH in position 8 of the GnRH-III sequence whereas in position 5 Boc-L-Lys(ε-Z)-OH is employed instead of Boc-His(Tos)-OH as protected amino derivative. The purification is accomplished by using the method of Example 26. A crude product is obtained in a yield of 335 g (with a chemical purity of about 80%); $R_{f2}$=0.55.

EXAMPLE 30

Preparation of Lys$^4$[Lys(ε-Fmoc)]$^8$-GnRH-III

By using 1 mmol of BHA resin Example 26 is followed with the difference that Boc-Lys(ε-Fmoc)-OH is used as protected amino acid in position 8 and Boc-Lys(ε-Z)-OH in position 4 of the peptide. After being purified on Sephadex G-25 column, the crude peptide is obtained in a yield of 1.04 g, with a purity of 80%; $R_{f2}$=0.29.

For purification, a solution containing 550 mg of crude product in 20% by volume acetic acid was applied onto a MPLC column according to Example 27 and eluted first with 200 ml of 20% by volume acetic acid (isocratic elution) and then purified by using gradient elution using 400 ml each of the following solutions: Solution A: 20% by volume acetic acid. Solution B: a 3:1 mixture of solution A and isopropanol. The fractions are collected and lyophilized to result in a yield of 217 mg of the aimed product; $R_{f2}$=0.45, $R_{f7}$=200.18.

EXAMPLE 31

Preparation of Lys$^4$-GnRH-III

To a solution of 200 mg of the crude peptide obtained in Example 31 in 10 ml of DMF, 15 ml of DMF containing 10% of piperidine are added under cooling with ice-water. One hour later the reaction mixture is evaporated and the residue is purified by using MPLC and gradient elution with 25% acetic acid up to a 2:1 mixture of 25% acetic acid and methanol. Thus, 68 mg of a pure product are obtained which proved to be uniform on the basis of TLC and HPLC analysis; $R_{f1}$=0.5, $R_{f2}$=0.67, $R_{f3}$=0.05.

EXAMPLE 32

Preparation of [Lys(ι-Ac)1]$^4$-GnRH-III

To a solution containing 200 mg of crude peptide obtained in Example 31 in 30 ml of DMF, DIVA and 130 mg of imidazole are added, then the mixture of 5 ml of dichloromethane (DCM) and 200 μl of acetic acid anhydride are dropped thereto under stirring and cooling. After one hour the reaction mixture is evaporated under reduced pressure. The residue is triturated with diethyl ether, the ethereal supernatant is decanted and the residue is dissolved in 15 ml of DMF. Then 2 ml of DMF containing 200 μl of piperidine are added and one hour later it is evaporated. The residue is dissolved in 20% acetic acid and purified by using MPLC method. The elution is carried out by using gradient elution (composed of 20% acetic acid and a 6:4 mixture of 10% acetic acid and methanol) to give 70 mg of a pure product which proved to be uniform on the basis of TLC and HPLC analysis; $R_{f2}$=0.067, $R_{f7}$=0.087.

EXAMPLE 33

Preparation of Glu$^6$-GnRH-III

Example 26 is followed with the difference that Boc-Glu-25-(OChx)-OH is used as protected amino acid in position 6 of the GnRH-III sequence. The purification is accomplished according to Example 2 by using gradient elution in ammonium acetate buffer solution. Characteristic values of the product: $R_f$=18 0.19, $R_{f7}$=0.086.

EXAMPLE 34

Preparation of Cyclo[Asp$^6$-Lys$^8$]-GnRH-III

After preparing hydrochloride salt according to Example 28 by using the lamprey GnRH-III decapeptide as starting substance, the cyclization is carried out according to Example 28. The product is purified according to Example 27.

EXAMPLE 35

Preparation of D-Ala$^{10}$-GnRH-III

Example 26 is followed with the difference that, instead of Boc-Gly-OH, Boc-D-Ala-OH protected amino acid is coupled as first amino acid to the benzhydrylamine resin. The purification is accomplished according to Example 27.

EXAMPLE 36

Preparation of H-D-Trp$^1$,[Lys($\epsilon$-Fmoc)]$^8$,D-Ala$^{10}$-GnRH-III

Example 26 is followed with the difference that in the GnRH-III sequence Boc-D-alanine is coupled as first amino acid: in the case of lysine of position 8 Boc-Lys($\epsilon$-Fmoc)-OH protected amino acid and to the N-terminal of the decapeptide Boc-D-Trp-OH protected amino acid are coupled. The purification is accomplished according to Example 26 on Sephadex G-25 column. The intermediary derivative is purified by using gradient elution according to Example 26.

EXAMPLE 37

Preparation of Ac-D-Trp$^1$,D-Ala$^{10}$-GnRH-III

From the protected peptide-BHA resin prepared according to Example 36 the Boc group is removed according to Example 26, then the peptide-BHA resin having a free amino terminal is acetylated with a mixture containing acetic acid anhydride and imidazole. Thereafter, the aimed peptide is cleaved from the resin by liquid HF according to Example 1, the protecting group is split off according to Example 32, and the product is purified according to Example 27.

EXAMPLE 38

Preparation of H-D-Trp$^1$,D-Ala$^{10}$-GnRH-III

The Fmoc protective group is removed according to Example 32 from the protected intermediary peptide prepared according to Example 36. Then the purification of the crude product is carried out by following Example 27.

EXAMPLE 39

Preparation of [Trp(For-Ind)]$^{3,7}$-GnRH-III

Example 26 was followed with the difference that in position 8 of the GnRH-III sequence Boc-Lys($\epsilon$-Z)-OH, in positions 3 and 7 Boc-Trp(For-Ind)-H protected amino acid derivative are used. The purifications are carried out by following Example 26.

EXAMPLE 40

Preparation of Phe$^7$-GnRH-III

Example 26 was followed with the difference that Boc-phenylalanine is used in position 7 of the GnRH-III sequence. The purification is carried out by following Example 26.

EXAMPLE 41

Preparation of GnRH-III(1-9)-ethylamide

According to the GnRH-III sequence the protected amino acid is coupled by starting from 1.46 mmol of Boc-Pro-Merrifield resin by following Example 26. The peptide protected on its side chains is cleaved from the resin by stirring it with a 20% by volume ethylamine solution in DMF at 10° C. for 48 hours. $R_{f2}$=0.5.

After evaporating DMF under reduced pressure, the residue is triturated with diethyl ether. The protective groups of the side chain are removed from the crude protected peptide by using liquid hydrogen fluoride according to Example 26. The crude peptide 16 is purified first on a Sephadex G-25 column followed by medium pressure liquid chromatography to give 215 mg of the aimed product, $R_{f2}$=0.31.

EXAMPLE 42

Preparation of Lys$^5$-D-Trp$^6$-hGnRH

Starting from 0.5 mmol of BHA resin and following the method of Example 26, as protected amino acids Boc-D-Trp-OH is used for the synthesis instead of Boc-Gly in position 6 and Boc-L-Lys($\epsilon$-Z)-OH instead of Boc-L-Tyr (Bzl)-OH in position 5 according to the sequence of amino acids of human GnRH. The purification is carried out according to Example 1 by using Sephadex G-25. The gradient elution is performed with 400 ml each of the following solutions: A: 70% by vol. of 0.05 M ammonium acetate solution (pH 4.00) and 30% by vol. of methanol 25 B: 30% by vol. of 0.05 M ammonium acetate solution (pH 4.00) and 70% by vol. of methanol. The solution obtained is lyophilized 3 times for removing the ammonium acetate to give 52 mg of the aimed 21 product; $R_{f2}$=0.34, $R_{f7}$=0.21.

EXAMPLE 43

Preparation of Lys$^4$,D-Trp$^6$-hGnRH

Example 26 is followed according to the amino acid sequence of hGnRH with the difference that in position 6 Boc-D-Trp-OH is used, and in position 4 Boc-L-Lys($\epsilon$-Z)-OH protected amino acid derivative is used instead of Boc-L-Ser(Bzl)-OH. The purification of the product is performed also according to Example 42 to obtain 60 mg of pure product.

EXAMPLE 44

Preparation of H-Glu$^1$,D-Trp$^6$-hGnRH

Example 26 is followed according to the amino acid sequence of hGnRH with the difference that in position 6 Boc-D-Trp-OH is used instead of Boc-glycine whereas in position 1 Boc-L-Glu(OChx)-OH protected amino acid derivative is used instead of pyroglutamic acid. The product is purified according to Example 42, except that after the gradient elution with ammonium acetate a step of making free from salts is inserted, wherein the gradient elution is carried out on MPLC column by using 300 ml each of the following solutions: Solution A: 20% by volume acetic acid; Solution B: a 3:1 mixture of solution A and isopropanol. The pure fractions are collected and lyophilized to give 53 mg of the aimed product; $R_{f1}$=0.29; $T_{f17}$=0.19.

EXAMPLE 45

Preparation of Lys$^5$,D-Phe$^6$-hGnRH(1-9)-ethylamide 22

According to Example 41 Boc-Pro-Merrifield resin is used as starting material but the synthesis is carried out according to the sequence of human GnRH, except that in position 6 Boc-P-Phe-OH and in position 5 Boc-Lys($\epsilon$-Z)-OH are used as protected amino acids. The peptide is cleaved from the resin by stirring in ethylamine at 0° C. for 8 hours, then stirring at room temperature overnight while ethylamine evaporates. Thereafter, the protected nonapeptide ethylamide is dissolved from the resin by washing with methanol and DMF. The solution obtained is evaporated and the residue is triturated with ether until it solidifies. The product obtained is treated with liquid HF according to Example 26, then the product is purified by HPLC method according to Example 27.

EXAMPLE 46

Preparation of Lys$^4$,D-Phe$^6$-hGnRH(1-9)ethylamide

Example 45 is followed with the difference that Boc-Lys (ε-Z)-OH is used as protected amino acid in position 4.

EXAMPLE 47

Preparation of Lys$^5$,D-Cpa$^6$-hGnRH(1-9)ethylamide

Example 45 is followed with the difference that instead of Boc-D-Phe-OH Boc-D-Cpa-OH is used as protected amino acid in position 6.

Human Cell Lines Used In The In Vitro Experiments

MCF-7 human mammary carcinoma cell line was stabilized in 1973 by Soule et al. [J. National Cancer Inst., 51, 1409–1416] from the pleural fluid of a patient suffering from mammary carcinoma. MDA-MB-231 human mammary carcinoma cell line was isolated and stabilized by Cailleau et al. [J. National Cancer Inst., 53, 661–674] in 1974 similarly from pleural fluid. Both cell lines grow in monolayer. MCF-7 and MDA-MB-231 human mammary carcinoma cell lines are maintained in plastic flasks (Greiner), in Dulbecco-modified Eagle-MEM (DMEM, GIBCO) liquid nutrient medium containing 10% of fetal calf serum. MCF-7 cell line is estradiol receptor (ER)-positive containing proteins specifically binding GnRH. Thus, it represents a useful model system for investigating the direct effect of GnRH mediated by the GnRH receptor. Being ER-negative and GnRH receptor-positive, MDA-MB-231 cell line is similarly suitable to study the direct effect of GnRH. PC3 human prostate carcinoma cell line was stabilized in cell culture by Kaighn et al. [Investigative Urology, 17, 16–23] in 1979. The cells are of epithelial type and form compact colonies in clonogenic assays. The Ishikawa cell line originates from human endometrial adenocarcinoina (M. Nishida et al.: Acta Obstet. Gynecol. Jpn. 37, 1103–1111 (1985)], it is epithelial in its character and contains steroid as well as GnRH receptors.

EXAMPLE 48

Dose-Survival With GnRH Analogues on MCF-7, MDA-MB-231 Human Mammary Carcinoma, PC3 Prostate Cancer and Ishikawa Endometrium Tumor Cell Cultures The examination gives accurate information about the cell-damaging effect of the substance tested as a function of varying doses. The treatment was carried out once; the colonies formed from the surviving cells were counted after 8–12 days. When using hormones, the substances were in general not toxic and possessed the great advantage of being cell- or receptor-specific, respectively. GnRH analogues were phase-specific, they inhibited but did not destroy the cells in G0/G1 phase. A part of the arrested cells again entered the cycle, an other part of them might be destroyed (apoptosis). The colonies formed from arrested cells did not achieve the countable colony size in the day of countingthe colonies (the colony number may be identical, the colony size cannot be identical). In the case of a dose-response investigation, colonies containing less than 15 cells were not counted. 300 cells were put into each Petri dishes of 3.5 cm in diameter. The treatment was once carried out 24 hours after setting, then the colonies formed were counted after 8–12 days. The cells were treated once after 24 hours with 1–50 μM of various GnRH analogues of Examples above or with 1–50 μM of GnRH-III, respectively. The percentages of inhibition obtained on MCF-7, MDA-MB-231, PC3 and Ishikawa cells, respectively, together with the dose of the active agent used are shown in Table VIII.

Based on these investigations, when used in a dose of 50 μM, the known synthetic GnRH-III peptide resulted in a 45% and 49% inhibition, respectively, of colony formation of MCF-7 and MDA-MB-231 cell cultures, respectively. Such a significant inhibition has not been observed until now by using any GnRH agonist (Ovurelin, Buserelin) or even GnRH antagonist (MI-1544). GnRH-III did not inhibit the Ishikawa cell line within the dose range used and it resulted only in a 21% inhibition of colony formation of the PC3 prostate cell culture. The effect of GnRH-III peptide was exceeded by the compound of Example 17 which caused an inhibition of 65% on MCF-7 and 63% on MDA-MB-231 (see Table VIII). Beside the compound of Example 42, the peptides of Examples 31 and 32 proved to be most effective (35–42%) on the MDA-MB-231 mammary carcinoma cell culture (Table VIII). On PC3 prostate tumour cell culture, the compound of Example 8 administered in a dose of 50 μM induced the strongest inhibition (31%) whereas compounds 6 and 7 did not influence and compound 17 weakly inhibited the colony-forming ability of the PC3 cell line within the dose range used (Table VIII). When employed in 50 μM dose on the Ishikawa endometrium tumour cell culture, the following results were achieved: 13% inhibition of colony formation by compound 3; 21% by compound 6; 14% by compound 7; 2% by compound 8; 15% by compound 17; and 24% by compound 14.

In these studies the D-Trp$^6$-hGnRH analogue (Sigma Co.) commonly used in the tumour therapy was employed as control. It appears from the data of Table VIII that, among the analogues tested, the analogues of Examples 26 and 40 showed a weak if any effect. Analogues 14 and 19 approximated the activity of the control. Other analogues (3, 6, 7 and 8) exceeded the inhibitory effect of control; analogue 17 resulted in a twice stronger inhibition.

EXAMPLE 49

Inhibition of the Cell Division Of Human Tumour Cell Lines

After being treated with trypsin, 300,000 each of MCF-7, MDA-MB-231, PC3 or Ishikawa cells, respectively, were passed into Petri dishes of 10 cm in diameter. Starting from the day following the setting, the cells were treated with 1–50 μM of the GnRH analogue in the exponential growth phase. During the experiment lasting for 5 days, the cells were treated in every two days with the peptide hormone dissolved in the nutrient medium, then the cell count was determined on the sixth day.

When used in 30 μM dose, GnRH-III exerted an inhibition of 35–40% both on MCF-7 as well as MDA-MB-231 cells. Based on these investigations, Ovurelin or Buserelin as hGnRH agonists did not induce a significant change in the cell count on the MCF-7 ER-positive cell line (5–15% inhibition) after 6 days' treatment; whereas they resulted in a 25–30% inhibition of cell proliferation on the DMA-MB-231 ER-negative cell line.

When used in a dose of 30 μM, the anti-proliferation effect of GnRH-III agreed with the direct antitumour effect of known GnRH antagonists (mammary GnRH derivatives containing several D-amino acids, MI-1892 and MI-1544) on both mammary tumour cell lines (Table IX). The proliferation-inhibiting effect of both substances 6 and 7 was nearly identical (27–31%) with the direct proliferation-inhibiting effect of GnRH antagonists containing several D-amino acids (MI-1544, MI-1892, SJ-1004) (Table IX).

As shown in Table IX, the proliferation-inhibiting effect of the substances, except compound 15, agreed with the results of inhibition of colony formation within certain limits. A close correlation exists between the inhibition of colony formation and the in vivo effectivity of the substances, too. The compositions of known peptides used as reference substances are as follows:

MI-1892:
   Ac-D-Trp$^{1,3}$,D-Cpa$^2$,Lys$^5$,[β-Asp(DEA)]$^6$,D-Ala$^{10}$-hGnRH

MI-1544:
   Ac-D-Trp$^{1,3}$,D-Cpa$^2$,D-Lys$^6$, D-Ala$^{10}$-hGnRH
   [M. Kovács et al., Peptides, 10, 925–931 (1989)]

SJ-1004:
   D-Phe$^2$, D-Trp$^3$, D-Lys$^6$-hGnRH

GnRH-III:
   pGlu-His-Trp-Ser-His-Asp-Trp-Lys-Pro-Gly-NH$_2$
   (SEQ ID NO:2)

Decapeptyl:
   pGlu-His-Trp-Ser-Tyr-D-Trp-Leu-Arg-Pro-Gly-NH$_2$
   (SEQ ID NO:6).

TABLE VIII

Inhibition of the colony formation on various human tumor cell lines

| Compound Example No. | Cell Line | Dose | % Inhibition |
|---|---|---|---|
| 2. Lys$^5$-GnRH-III | MCF-7 | 50 μM | 0 |
|  | MDA-MB-231 | 50 μM | 0 |
| 3. Lys$^5$-cyclo--(Asp$^6$,Lys$^8$)--GnRH-III | MCF-7 | 50 μM | 44 |
|  |  | 50 μM | 13 |
| 6. Lys$^4$-GnRH-III | MCF-7 | 10 μM | 15 |
|  |  | 50 μM | 40 |
|  | MDA-MB-231 | 10 μM | 18 |
|  |  | 50 μM | 35 |
|  | Ishikawa | 50 μM | 21 |
|  | PC3 | 50 μM | 0 |
| 7. [Lys(ε-Ac)]$^4$-GnRH-III | MCF-7 | 10 μM | 40 |
|  |  | 50 μM | 52 |
|  | MDA-MB-231 | 10 μM | 31 |
|  |  | 50 μM | 42 |
|  | Ishikawa | 50 μM | 14 |
|  | PC3 | 50 μM | 0 |
| 8. Glu$^6$-GnRH-III | MCF-7 | 50 μM | 44 |
|  | MDA-MB-231 | 50 μM | 25 |
|  | Ishikawa | 50 μM | 2 |
|  | PC3 | 50 μM | 31 |
| 17. Lys$^5$-DTrp$^6$-hGnRH | MCF-7 | 10 μM | 39 |
|  |  | 50 μM | 65 |
|  | MDA-MB-231 | 10 μM | 30 |
|  |  | 50 μM | 63 |
|  | Ishikawa | 50 μM | 17 |
|  | PC3 | 50 μM | 18 |
| 14. [Trp(For-Ind)]$^{3,7}$-GnRH-III | MCF-7 | 50 μM | 31 |
|  | Ishikawa | 50 μM | 24 |
| 15. Phe$^7$-GnRH-III | MCF-7 | 50 μM | 26 |
|  | MDA-MB-231 | 50 μM | 21 |
| 19. H-Glu$^1$,D-Trp$^6$-hGnRH | MCF-7 | 10 μM | 16.8 |
|  |  | 50 μM | 32.7 |
| D-Trp$^6$-hGnRH (Decapeptyl) | MCF-7 | 10 μM | 17.1 |
|  |  | 50 μM | 36.7 |

TABLE VIII-continued

Inhibition of the colony formation on various human tumor cell lines

| Compound Example No. | Cell Line | Dose | % Inhibition |
|---|---|---|---|
|  | MDA-MB-231 | 10 μM | 15.7 |
|  |  | 50 μM | 38.7 |

TABLE IX

GnRH analogue Inhibition of cell proliferation in human tumor cell lines

| Compound Example No. | Cell line | Dose | % Inhibition |
|---|---|---|---|
| MI-1544 | MCF-7 (2x) | 30 μM | 36 |
|  | MDA-MB-231 (2x) | 30 μM | 34 |
|  | Ishikawa (2x) | 30 μM | 8 |
|  | PC3 (2x) | 30 μM | 24 |
| MI-1892 | MCF-7 (2x) | 30 μM | 35 |
|  | MDA-MB-231 (2x) | 30 μM | 35 |
|  | Ishikawa (2x) | 30 μM | 14 |
|  | PC3 (2x) | 30 μM | 33 |
| SJ-1004 | MCF-7 (2x) | 30 μM | 17 |
|  | MDA-MB-231 (2x) | 30 μM | 23 |
|  | Ishikawa (2x) | 30 μM | 8 |
|  | PC3 (2x) | 30 μM | 10 |
| 6. Lys$^4$-GnRH-III | MCF-7 (2x) | 30 μM | 27 |
|  | MDA-MB-231 (2x) | 30 μM | 28 |
| 7. [Lys(ε-Ac)]$^4$-GnRH-III | MCF-7 (2x) | 30 μM | 31 |
| 8. Glu$^6$-GnRH-III | MCF-7 (2x) | 30 μM | 18 |
| 15. Phe$^7$-GnRH-III | MCF-7 (2x) | 30 μM | 0 |
| GnRH-III | MCF-7 (2x) | 30 μM | 40 |
|  | MDA-MB-231 (2x) | 30 μM | 39 |
|  | PC3 (2x) | 30 μM | 10 |
|  | Ishikawa (2x) | 30 μM | 8 |

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A compound selected from the group consisting of:

[Lys(ε-Fmoc)]$^5$-gonadotropin-releasing hormone (GnRH-III),

Lys$^5$-GnRH-III,

Lys$^5$,cyclo[Asp$^6$-Lys$^8$]-GnRH-III,

Lys$^5$,[Lys(ε-Fmoc)]$^8$-GnRH-III,

Lys$^4$,[Lys(ε-Fmoc)]$^8$-GnRH-III,

Lys$^4$-GnRH-III,

[Lys(ε-Ac)]$^4$-GnRH-III,

Glu$^6$-GnRH-III, cyclo[ASP$^6$-Lys$^8$]-GnRH-III,

D-Ala$^{10}$-GnRH)-III,

H-D-Trp$^1$,[Lys(ε-Fmoc)]$^8$, D-Ala$^{10}$-GnRH-III,

Ac-D-Trp$^1$, D-Ala$^{10}$-GnRH-III,

H-D-Trp$^1$, D-Ala$^{10}$-GnRH-III,

[Trp(For-Ind)]$^{3,7}$-GnRH-III,

Phe$^7$-GnRH-III,

GnRH-III(1-9)-ethylamide,

Lys$^5$, D-Trp$_6$-human gonadotropin-releasing hormone (hGnRH),

Lys$^4$, D-Trp$^6$-hGnRH,

H-Glu$^1$, D-Trp$^6$-hGnRH,

Lys$^5$, D-Phe$^6$-hGnRH(1-9)-ethylamide,

Lys$^4$, D-Phe$^6$-hGnRH(1-9)-ethylamide,

Lys$^5$, D-Cpa$^6$-hGnRH(1-9)-ethylanuide; as well as pharmaceutically acceptable salts and esters of these compounds.

2. A composition comipnsing a compound of claim 1 and a pharmaceutically acceptable carrier.

* * * * *

UNITED STATES PATENT AND TRADEMARK OFFICE
CERTIFICATE OF CORRECTION

PATENT NO. : 6,664,369 B1
DATED : December 16, 2003
INVENTOR(S) : Sandor Lovas et al.

It is certified that error appears in the above-identified patent and that said Letters Patent is hereby corrected as shown below:

Column 7,
Line 66, "[Lys(e-Ac)]$^4$" should be -- [Lys(ϵ-Ac)]$^4$ --

Column 8,
Line 13, "Trp" should be -- Trp$^6$ --

Column 9,
Line 47, "(Ha)" should be -- (IIa) --

Column 11,
Line 11, "(IIb)" should be -- (IIh) --

Column 19,
Line 9, "Ahx]$^5$" should be -- Ahx]}$^5$ --
Line 10, "(Dea)]}$^6$" should be -- (Dea)]$^6$ --
Line 21, "acid)-]}" should be -- acid)-]}$^5$ --

Column 30,
Line 39, "OC" should be -- O°C --

Column 32,
Line 29, "DIVA" should be -- DIEA --

Column 42,
Line 50, "Trp$_6$" should be -- Trp$^6$ --
Line 57, "ethylanuide" should be -- ethylamide --
Line 60, "comipnsing" should be -- comprising --

Signed and Sealed this

Twenty-seventh Day of July, 2004

JON W. DUDAS
*Acting Director of the United States Patent and Trademark Office*